(12) United States Patent
Kuboi et al.

(10) Patent No.: US 11,399,752 B2
(45) Date of Patent: Aug. 2, 2022

(54) ENZYME SENSOR AND ELECTRONIC DEVICE

(71) Applicants: SONY SEMICONDUCTOR SOLUTIONS CORPORATION, Kanagawa (JP); SONY CORPORATION, Tokyo (JP)

(72) Inventors: Nobuyuki Kuboi, Kanagawa (JP); Yoshiki Ebiko, Kanagawa (JP); Yoshio Goto, Kanagawa (JP)

(73) Assignees: SONY SEMICONDUCTOR SOLUTIONS CORPORATION, Kanagawa (JP); SONY CORPORATION, Tokyo (JP)

( * ) Notice: Subject to any disclaimer, the term of this patent is extended or adjusted under 35 U.S.C. 154(b) by 689 days.

(21) Appl. No.: 16/330,217

(22) PCT Filed: Aug. 9, 2017

(86) PCT No.: PCT/JP2017/028890
§ 371 (c)(1),
(2) Date: Mar. 4, 2019

(87) PCT Pub. No.: WO2018/066227
PCT Pub. Date: Apr. 12, 2018

(65) Prior Publication Data
US 2019/0216372 A1  Jul. 18, 2019

(30) Foreign Application Priority Data

Oct. 6, 2016  (JP) .............................. JP2016-197755

(51) Int. Cl.
*A61B 5/1486* (2006.01)
*C12Q 1/00* (2006.01)
(Continued)

(52) U.S. Cl.
CPC ............ *A61B 5/1486* (2013.01); *A61B 5/682* (2013.01); *A61C 13/10* (2013.01); *A61M 21/02* (2013.01);
(Continued)

(58) Field of Classification Search
CPC .......... A61C 13/10; A61M 2021/0022; A61M 2021/0077; A61M 2021/0027;
(Continued)

(56) References Cited

U.S. PATENT DOCUMENTS 9,795,326 B2 * 10/2017 Hoss ................. A61B 5/14865
2010/0206748 A1    8/2010 Morita et al.

FOREIGN PATENT DOCUMENTS

CA    2512380 A1   7/2004
CN    1739026 A    2/2006
(Continued)

OTHER PUBLICATIONS

Shitanda, et al., "Screen Printed Enzyme Electrodes Using Microcapsules Containing Glucose Oxidase and Mediator", vol. 76, Issue 8, 2008, pp. 569-572.
(Continued)

*Primary Examiner* — Christine H Matthews
*Assistant Examiner* — Joshua Daryl D Lannu
(74) *Attorney, Agent, or Firm* — Chip Law Group

(57) ABSTRACT

An enzyme sensor including a pair of electrodes, an electron transfer layer held between the pair of electrodes, and an electron generating capsule in which a membrane containing at least a substrate of an enzyme to be detected encloses at least one or more kinds of enzymes other than the enzyme to be detected, the electron generating capsule being in contact with the electron transfer layer.

15 Claims, 25 Drawing Sheets

(51) Int. Cl.
*A61B 5/00* (2006.01)
*A61C 13/10* (2006.01)
*A61M 21/02* (2006.01)
*G01N 27/327* (2006.01)
*G01N 27/416* (2006.01)
*A61M 21/00* (2006.01)

(52) U.S. Cl.
CPC ............... *C12Q 1/00* (2013.01); *C12Q 1/002* (2013.01); *C12Q 1/005* (2013.01); *G01N 27/3271* (2013.01); *G01N 27/3272* (2013.01); *G01N 27/416* (2013.01); *A61M 2021/005* (2013.01); *A61M 2021/0022* (2013.01); *A61M 2021/0027* (2013.01); *A61M 2021/0077* (2013.01); *A61M 2205/3303* (2013.01)

(58) Field of Classification Search
CPC .......... A61M 2205/3303; A61M 21/02; A61M 2021/005; A61B 5/14507; A61B 5/1455; A61B 5/6803; A61B 5/1486; A61B 5/14546; A61B 5/682; C12Q 1/26; C12Q 1/34; C12Q 1/005; C12Q 1/002; C12Q 1/40; C12Q 1/00; G01N 27/3271; G01N 27/416; G01N 2333/904; G01N 27/3272; G01N 2333/926
See application file for complete search history.

(56) References Cited

FOREIGN PATENT DOCUMENTS

| | | |
|---|---|---|
| CN | 101779122 A | 7/2010 |
| EP | 2180315 A1 | 4/2010 |
| EP | 3196778 A1 | 7/2017 |
| JP | 60-093344 A | 5/1985 |
| JP | 10-262645 A | 10/1998 |
| JP | 2002-168860 A | 6/2002 |
| JP | 2006-512573 A | 4/2006 |
| WO | 2004/059310 A1 | 7/2004 |
| WO | 2009/017188 A1 | 2/2009 |
| WO | 2016/042908 A1 | 3/2016 |

OTHER PUBLICATIONS

International Search Report and Written Opinion of PCT Application No. PCT/JP2017/028890, dated Nov. 14, 2017, 09 pages of ISRWO.

Shitanda, et al., "Screen printed Enzyme Electrodes Using Microcapsules Containing Glucose Oxidase and Mediator", pp. 569-572.

Office Action for JP Patent Application No. 2018-543757, dated May 11, 2021, 02 pages of English Translation and 02 pages of Office Action.

Shitanda, et al., "Screen-printed Enzyme Electrodes Using Microcapsules Containing Glucose Oxidase and Mediator", Electrochemistry, vol. 76, No. 8, 2008, pp. 569-572.

* cited by examiner

ENZYME SENSOR AND ELECTRONIC DEVICE

CROSS REFERENCE TO RELATED APPLICATIONS

This application is a U.S. National Phase of International Patent Application No. PCT/JP2017/028890 filed on Aug. 9, 2017, which claims priority benefit of Japanese Patent Application No. JP 2016-197755 filed in the Japan Patent Office on Oct. 6, 2016. Each of the above-referenced applications is hereby incorporated herein by reference in its entirety.

TECHNICAL FIELD

The present disclosure relates to an enzyme sensor and an electronic device.

BACKGROUND ART

In recent years, advances in medical research have revealed that the amount of a secreted enzyme changes depending on a mental or physical state in the living body.

Thus, it is considered that a disease or the like is prevented from being caused by measuring a component of the body fluid (e.g., saliva, blood, etc.) of the subject to grasp the mental or physical state of the subject and detect a symptom of the disease or the like. For achieving such a goal, an enzyme sensor capable of simply and accurately measuring the component of the body fluid of the living body is demanded.

For example, the following Patent Literature 1 discloses an enzyme sensor that estimates the mental state of the user by detecting the amount of amylase contained in the saliva thorough an optical method. Further, the following Patent Literature 1 makes disclosure on leading the mental state of the user to the specific state on the basis of the mental state of the user estimated by the enzyme sensor.

CITATION LIST

Patent Literature

Patent Literature 1: WO 2016/042908

DISCLOSURE OF INVENTION

Technical Problem

However, the enzyme sensor disclosed in the above Patent Literature 1 measures the amount of the enzyme by optically detecting the accumulated amount of a coloring substance generated by an irreversible reaction of the enzyme, thus it is difficult to accurately measure the fluctuation of the enzyme amount.

Thus, the present disclosure proposes a new and improved enzyme sensor and electronic device capable of accurately measuring the amount of an enzyme contained in the body fluid of the living body.

Solution to Problem

According to the present disclosure, there is provided an enzyme sensor including: a pair of electrodes; an electron transfer layer held between the pair of electrodes; and an electron generating capsule in which a membrane containing at least a substrate of an enzyme to be detected encloses at least one or more kinds of enzymes other than the enzyme to be detected, the electron generating capsule being in contact with the electron transfer layer.

In addition, according to the present disclosure, there is provided an electronic device including: an enzyme sensor that includes a pair of electrodes, an electron transfer layer held between the pair of electrodes, and an electron generating capsule in which a membrane containing at least a substrate of an enzyme to be detected encloses at least one or more kinds of enzymes other than the enzyme to be detected, the electron generating capsule being in contact with the electron transfer layer; a determination portion that determines a state of a wearing subject wearing the enzyme sensor on the basis of an amount of the enzyme detected by the enzyme sensor; and a driving portion that performs driving on the basis of the determined state of the wearing subject.

According to the present disclosure, it becomes possible to convert the presence of the enzyme to be detected to an electric current by a reversible mechanism in which an electron is accepted by and released from an electrolyte.

Advantageous Effects of Invention

As described above, according to the present disclosure, the amount of the enzyme contained in the body fluid of the subject can be more accurately measured.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
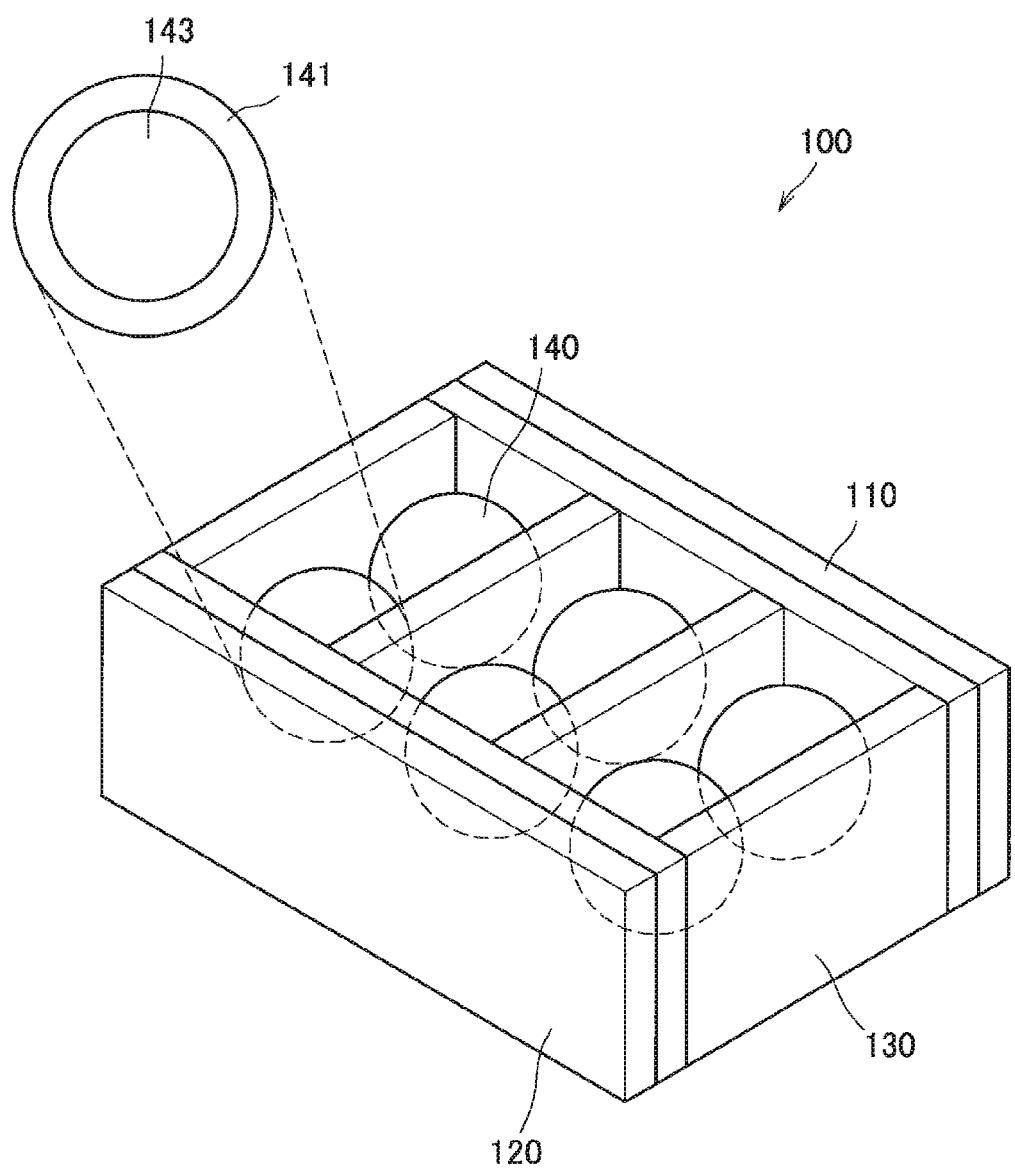
FIG. 1 is a perspective view illustrating an exemplary structural of a sensor portion of an enzyme sensor according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that descriptions will be given in the following order.
0. Background leading to technique according to present disclosure
1. First embodiment
  1.1. Exemplary structure of sensor portion of enzyme sensor
  1.2. Exemplary configuration of control of enzyme sensor
  1.3. Exemplary operation of enzyme sensor
  1.4. Production method of enzyme sensor
2. Second embodiment
3. Specific examples
3.1. First specific example
3.2. Second specific example
3.3. Third specific example
4. Summary

0. Background Leading to Technique According to Present Disclosure

Figure 2:
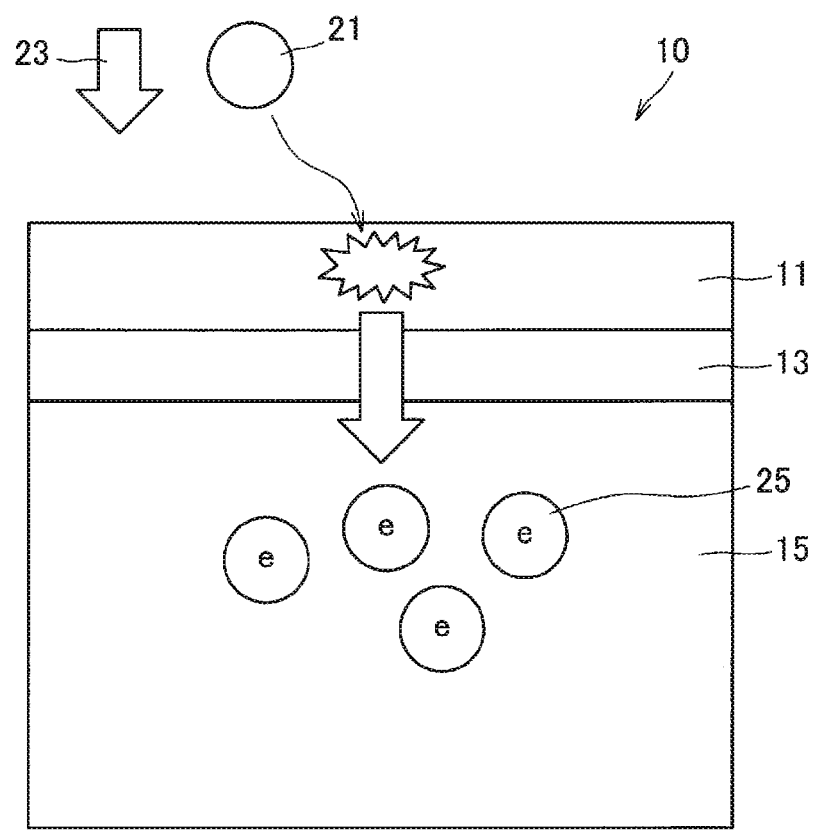
FIG. 2 is a schematic view illustrating an outline of an amylase sensor using an optical method.

First, a description is given of the background allowing the present inventors to reach the technique according to the present disclosure with reference to FIG. 2.

In recent years, advances in medical research have revealed that the amount of an enzyme contained in the body fluid changes depending on a mental or physical state in the living body. For example, amylase, which is an enzyme contained in the saliva, is found to increase by the mental stress.

In modern society, the mental stress is known as a factor that exerts a serious influence on health. For example, depression caused by the enormous mental stress is accompanied by a physical symptom such as sleeplessness, excessive sleepiness, loss of appetite, overeating, headache, and fatigue feeling, and, consequently, causes a decline in motivation for work, a further onset of a disease, and the like. Further, once the depression is developed, the symptom can be reduced by the treatment, however, it is difficult to completely cure the depression. Thus, it is socially demanded to detect the causative mental stress and control the exposure amount of the mental stress in order to prevent the depression and maintain and manage health.

The enzyme described herein is easily inactivated by oxygen and the like, thus the amount of the enzyme is desirably measured by detecting the enzyme at its secretion site in real time. For example, in a case of detecting the amount of amylase, the amount of the amylase contained in the saliva is desirably detected in the oral cavity in real time.

Specifically, consideration is given to an amylase sensor using an optical method shown in FIG. 2. FIG. 2 is a schematic view illustrating an outline of an amylase sensor 10 using an optical method.

As shown in FIG. 2, the amylase sensor 10 has a structure in which a photodiode 15, a color filter 13, and a chromogen layer 11 are sequentially laminated.

The chromogen layer 11 includes a substance that generates a coloring substance by an enzyme reaction with amylase 21. For example, the chromogen layer 11 includes 2-chloro-4-nitrophenyl-4-galactopyranosylmaltoside (Gal-G2-CNP). Gal-G2-CNP contained in the chromogen layer 11 is hydrolyzed by the amylase 21 to release 2-chloro-4-nitrophenol (CNP) exhibiting a yellow color. Thus, the amylase sensor 10 can estimate the amount of the amylase 21 by measuring a change quantity of CNP per unit time by an optical method using the photodiode 15.

The color filter 13 is a film that transmits light only in the wavelength band corresponding to a specific color. For example, the color filter 13 is a film that transmits yellow light and absorbs light of other colors. In this manner, the color filter 13 separates the light in the wavelength band corresponding to the yellow color exhibited by the released CNP from background light 23.

The photodiode 15 is a photoelectric conversion element that converts the light transmitted through the color filter 13 to an electron 25. For example, the photodiode 15 is configured from silicon (Si) doped with an impurity. Note that the photodiode 15 is equipped with an analog-to-digital (AD) converter that converts an analog signal generated by the photodiode 15 to a digital signal, an amplifier that amplifies the converted digital signal, and the like.

In the amylase sensor 10 having such a configuration, Gal-G2-CNP contained in the chromogen layer 11 is first hydrolyzed by the amylase 21 to release CNP, thereby causing a color change of the chromogen layer 11 from white to yellow. Next, the photodiode 15 performs the photoelectric conversion in accordance with the intensity of the yellow color exhibited by the chromogen layer 11 under the background light 23, resulting in conversion of a photon to the electron 25. In this manner, the amylase sensor 10 can measure the change quantity of the intensity of the yellow color exhibited by the chromogen layer 11 per unit time and thus can measure the amount of the amylase 21.

However, in the amylase sensor 10 shown in FIG. 2, the amylase 21 and Gal-G2-CNP undergo the irreversible reaction, thus CNP accumulates in the chromogen layer 11 as the measurement is continued, making it difficult to accurately measure a reduction in the amount of the amylase 21 using the amylase sensor 10 shown in FIG. 2.

Further, the background light 23 emitted from a light emitting element or the like is required for the photodiode 15 to detect the yellow light of CNP in the dark oral cavity as CNP does not spontaneously emit the light. Arranging the light emitting element in the amylase sensor 10 for this reason increases the size of the device and thus makes it difficult to wear the device in the oral cavity for a long time without having an uncomfortable feeling.

Thus, the enzyme sensor with a small and simple structure capable of measuring the enzyme amount at the enzyme secretion site in real time has been demanded. Further, the mechanism for converting the enzyme amount to the detection signal by the enzyme sensor is desirably reversible for accurately measuring the enzyme amount.

As a result of the extensive investigation of the above requirement and the like, the present inventors have found the technique according to the present disclosure. In the present disclosure, proposed are an enzyme sensor with a simple structure capable of more accurately measuring the amount of an enzyme, and an electronic device that performs driving on the basis of information measured by the enzyme sensor.

1. First Embodiment (1.1. Structure of Sensor Portion of Enzyme Sensor)

First, an exemplary structure of a sensor portion arranged in an enzyme sensor according to a first embodiment of the present disclosure will be described with reference to FIG. 1. FIG. 1 is a perspective view illustrating an exemplary structural of a sensor portion 100 of the enzyme sensor according to the first embodiment of the present disclosure.

As shown in FIG. 1, the sensor portion 100 of the enzyme sensor according to the present embodiment includes a pair of electrodes 110 and 120, an electron transfer layer 130 held between the pair of electrodes 110 and 120, and an electron generating capsule 140 retained inside a concave structure of the electron transfer layer 130.

The pair of electrodes 110 and 120 functions as an output portion that extracts an electron generated by a reaction with an enzyme to be detected as a detection signal. Specifically, the pair of electrodes 110 and 120 can extract the electron generated in the electron generating capsule 140 via the electron transfer layer 130 by applying a voltage between the electrodes.

For example, the pair of electrodes 110 and 120 may be prepared using a material having conductivity and formed as a pair of parallel flat plates holding the electron transfer layer 130 therebetween. Specifically, the pair of electrodes 110 and 120 may be formed of a single metal substance such as copper (Cu), silver (Ag), platinum (Pt), aluminum (Al), tungsten (W), or titanium (Ti), or an alloy thereof. They may be formed of a carbon material such as graphite or amorphous carbon. However, the sensor portion 100 of the enzyme sensor is worn so as to be in contact with the body fluid of the living body, thus the pair of electrodes 110 and 120 may be formed of the metal in which corrosion such as rust hardly occurs or the carbon material.

Note that one of the pair of electrodes 110 and 120 functions as an anode and the other functions as a cathode, however, the polarity of the pair of electrodes 110 and 120 can be appropriately set in accordance with a direction of extracting the detection signal.

The electron transfer layer 130, which is in contact with the electron generating capsule 140 and held between the pair of electrodes 110 and 120, transfers the electron generated in the electron generating capsule 140 to one of the electrodes 110 and 120 (i.e., the anode). Specifically, the electron transfer layer 130 contains an electrolyte capable of accepting an electron and transmits the electron to the anode side of the electrodes 110 and 120 using the electrolyte. For example, the electron transfer layer 130 may be formed by gelatinating a solution containing the electrolyte.

The electrolyte contained in the electron transfer layer 130 is not particularly limited as long as it is a substance capable of reversibly accepting and releasing the electron, and a known substance, for example, a ferricyanide ion, may be used. The ferricyanide ion ($[Fe(CN)_6]^{3-}$) is an electrolyte that is reversibly changeable into an ferrocyanide ion ($[Fe(CN)_6]^{4-}$) by an oxidation and reduction reaction. That is, the ferricyanide ion ($[Fe(CN)_6]^{3-}$) is converted to the ferrocyanide ion ($[Fe(CN)_6]^{4-}$) by accepting the electron, and the ferrocyanide ion ($[Fe(CN)_6]^{4-}$) can be returned to the ferricyanide ion ($[Fe(CN)_6]^{3-}$) by releasing the electron to one of the electrodes 110 and 120. Note that, as the electrolyte contained in the electron transfer layer 130, benzoquinone or the like can be used other than the ferricyanide ion.

Further, in the electron transfer layer 130, at least one or more concave structures may be arranged in a surface not being held between the pair of electrodes 110 and 120, and the electron generating capsule 140 may be retained in the concave structure. Arranging the concave structure in the electron transfer layer 130 allows the electron transfer layer 130 to securely retain the electron generating capsule 140. Further, the electron transfer layer 130 can increase the contact area with the electron generating capsule 140.

Note that a plurality of the concave structures may be arranged in the electron transfer layer 130 and a plurality of the electron generating capsules 140 may be retained in the concave structure. For example, increasing the number of the concave structures can increase the contact area between the electron transfer layer 130 and the electron generating capsule 140. Further, increasing the number of the electron generating capsules 140 in the concave structure can increase reaction sites between amylase and the electron generating capsules 140. The number of the concave structures arranged in the electron transfer layer 130 and the number of the electron generating capsules 140 arranged inside the concave structure can be appropriately set.

The electron generating capsule 140 includes the reaction site where the electron is generated by the enzymatic reaction with the enzyme to be detected and generates the electron in accordance with the amount of the enzyme to be detected. Specifically, the electron generating capsule 140 has a structure in which a content liquid 143 containing at least one or more kinds of the enzymes other than the one to be detected is enclosed by an outer membrane 141 containing at least a substrate of the enzyme to be detected.

The outer membrane 141 contains the substrate of the enzyme to be detected and functions as the reaction site between the enzyme to be detected and the sensor portion 100 of the enzyme sensor. Thus, the shape of the electron generating capsule 140 formed by the outer membrane 141 may be a substantially spherical shape so that the area of the surface serving as the reaction site with the enzyme to be detected becomes larger.

Further, the outer membrane 141 has a function of keeping the content liquid 143 inside the electron generating capsule 140 to prevent the content liquid 143 from leaking outside the sensor portion 100. For this purpose, the outer membrane 141 may include a lipid, a protein, a carbohydrate, or the like in addition to the substrate of the enzyme to be detected as a membrane constituting component in order to enhance the strength of the membrane.

The enzyme contained in the content liquid 143 includes at least an oxidase. Further, a substrate of the oxidase is a product generated by the enzymatic reaction of the substrate contained in the outer membrane 141 through at least one or more steps. In this case, the oxidase can oxidize the product generated by the reaction of the enzyme to be detected to extract the electron from the product. Further, the enzyme contained in the content liquid 143 may further include another enzyme using the product of the reaction between the enzyme to be detected and the substrate contained in the outer membrane 141 as the substrate. In this case, the oxidase contained in the content liquid 143 use the final product of the multi-step reactions performed by the enzyme to be detected and another enzyme contained in the content liquid 143 as the substrate.

Further, the content liquid 143 may further include a solvent for dissolving the enzyme (e.g., water, etc.), a functional polymer for stabilizing the enzyme, and the like. For example, the content liquid 143 may further include a water-dispersion solution of PMEH (a copolymer of 2-(methacryloyloxy) ethyl phosphorylcholine and 2-ethylhexyl methacrylate) having high biocompatibility.

Specifically, the reaction between the electron generating capsule 140 and the enzyme to be detected proceeds as follows. First, the enzyme to be detected and the substrate contained in the outer membrane 141 are reacted to produce an enzymatic reaction product of the substrate. Then, the enzymatic reaction product thus produced is oxidized by the oxidase, which is contained in the content liquid 143 and oozes out from the inside of the content liquid 143 by the difference of the osmotic pressure, to release the electron. The electron thus released is accepted by the electrolyte contained in the electron transfer layer 130 and extracted by one of the electrodes 110 and 120 as described above.

For example, in a case where the enzyme to be detected is amylase, the outer membrane 141 of the electron generating capsule 140 may be configured by including at least starch as the substrate of the amylase and the content liquid 143 may be configured by including at least maltase and glucose oxidase.

In such a case, first, the amylase to be detected and the starch contained in the outer membrane 141 are reacted to produce maltose. Next, the maltase, which is contained in the content liquid 143 and oozes out to the outer membrane 141 by the difference of the osmotic pressure, and the maltose are reacted to produce glucose. Subsequently, the glucose oxidase contained in the content liquid 143 and the glucose are reacted to extract the electron from the glucose. Further the electron extracted from the glucose is accepted by the ferricyanide ion or the like contained in the electron transfer layer 130. In this manner, the ferricyanide ion is converted to the ferrocyanide ion.

The above reactions are represented by the following chemical formulas 1 and 2.

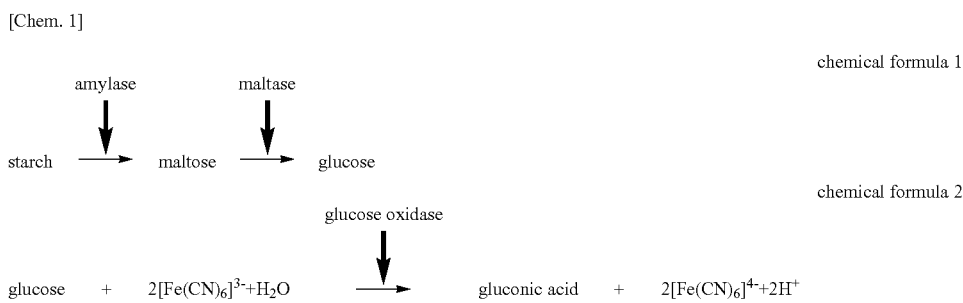

According to the enzyme sensor including the sensor portion 100 having the structure described above, the enzyme to be detected can be detected until the substrate contained in the outer membrane 141 of the electron generating capsule 140 is consumed by the reaction of the enzyme to be detected.

Further, the sensor portion 100 may further include an ion exchange membrane that covers at least an opening of the concave structure of the electron transfer layer 130. The ion exchange membrane prevents the content liquid 143 of the electron generating capsule 140, the electrolyte contained in the electron transfer layer 130, or the like from leaking from the sensor portion 100 to the body fluid.

In the sensor portion 100, for example, the content liquid 143 enclosed by the outer membrane 141 may leak by the consumption of the substrate contained in the outer membrane 141 of the electron generating capsule 140 or the electrolyte contained in the electron transfer layer 130 may elute by the water content contained in the body fluid. Thus, the sensor portion 100 brought into contact with the body fluid may further include the ion exchange membrane that covers the electron transfer layer 130 to prevent the content liquid 143 and the electrolyte from leaking to the body fluid. Even if the ion exchange membrane is provided, the sensor portion 100 can still perform the reaction between the enzyme to be detected and the electron generating capsule 140 through the ion exchange membrane.

Note that, in a case where the electrolyte contained in the electron transfer layer 130 is a negative ion (e.g., the ferricyanide ion), a cation exchange membrane may be used as the ion exchange membrane for preventing the leakage of the electrolyte contained in the electron transfer layer 130. Further, in a case where the electrolyte contained in the electron transfer layer 130 is a positive ion, an anion exchange membrane may be used as the ion exchange membrane.

(1.2. Exemplary Configuration of Control of Enzyme Sensor)

Figure 3:
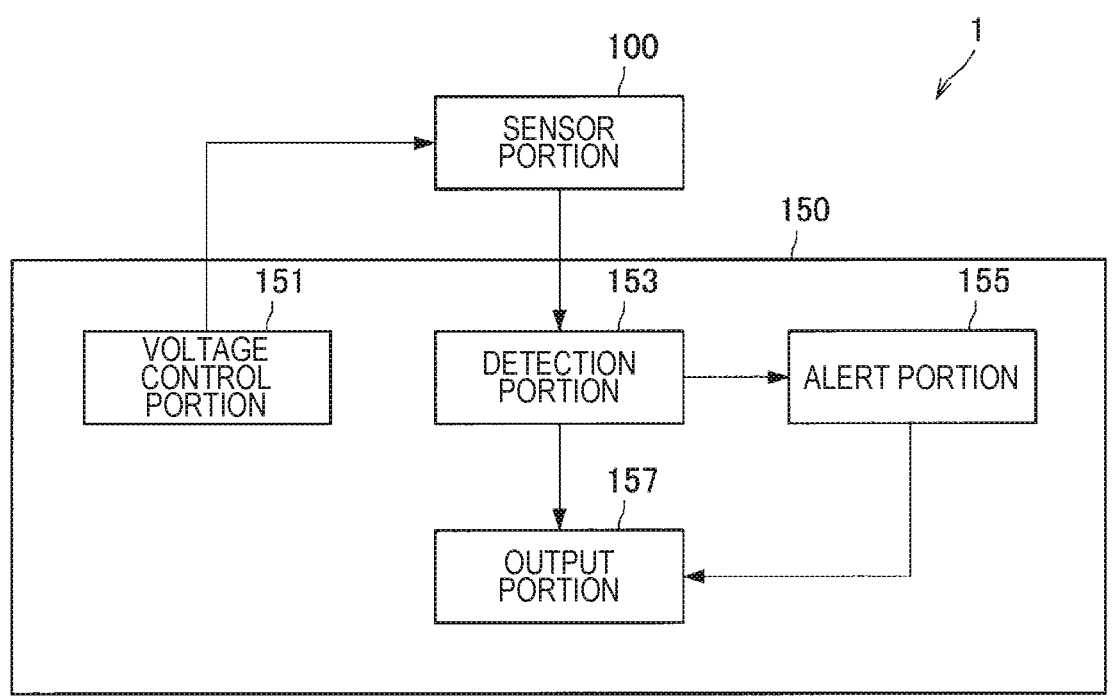
FIG. 3 is a block diagram illustrating an exemplary configuration of a control of the enzyme sensor according to the first embodiment of the present disclosure.

Next, an exemplary configuration of a control of the enzyme sensor according to the present embodiment will be described with reference to FIG. 3 to FIG. 5. FIG. 3 is a block diagram illustrating an exemplary configuration of the control of the enzyme sensor 1 according to the present embodiment.

As shown in FIG. 3, the enzyme sensor 1 includes the sensor portion 100 shown in FIG. 1 and a logic portion 150 for controlling the sensor portion 100. Further, the logic portion 150 includes a voltage control portion 151, a detection portion 153, an alert portion 155, and an output portion 157.

The sensor portion 100 has been described above with reference to FIG. 1, thus each configuration of the logic portion 150 will be described below. Note that the logic portion 150 is achieved, for example, by the cooperation of a hardware such as a CPU (central processing unit), a RAM (random access memory), and a ROM (read only memory) and a software that controls the operation of each configuration.

The voltage control portion 151 controls the voltage applied between the pair of electrodes 110 and 120 of the sensor portion 100 in order to measure the amount of the enzyme to be detected. Specifically, the voltage control portion 151 controls the voltage so as to apply a rectangular pulse voltage between the pair of electrodes 110 and 120.

The detection portion 153 detects the amount of the enzyme to be detected by measuring an electric current flowing between the pair of electrodes 110 and 120 of the sensor portion 100. Specifically, when the rectangular pulse voltage is applied between the electrodes 110 and 120 by the voltage control portion 151, the electrolyte which has accepted the electron in the electron transfer layer 130 (e.g., the ferrocyanide ion) releases the electron to the electrode at the anode side and is returned to the electrolyte before accepting the electron (e.g., the ferricyanide ion). During this time, the released electron causes the flow of the electric current between the pair of electrodes 110 and 120.

In this manner, the detection portion 153 can detect the amount of the electrolyte which has accepted the electron (e.g., the ferrocyanide ion) by detecting the level of the electric current flowing between the pair of electrodes 110 and 120. Further, the amount of the electrolyte which has accepted the electron (e.g., the ferrocyanide ion) depends on the amount of the reaction between the enzyme to be detected and the electron generating capsule 140, thus the detection portion 153 can calculate the amount of the enzyme to be detected from the level of the electric current flowing between the pair of electrodes 110 and 120.

Here, the voltage application by the voltage control portion 151 and the electric current detection by the detection portion 153 will be more specifically described with reference to FIG. 4. FIG. 4 is a graph diagram illustrating a relationship between the voltage applied to the pair of electrodes 110 and 120 of the sensor portion 100 and the electric current. Note that, for the sake of simplicity, the description is given of a case where the electrolyte contained in the electron transfer layer 130 is the ferricyanide ion below.

Figure 4:
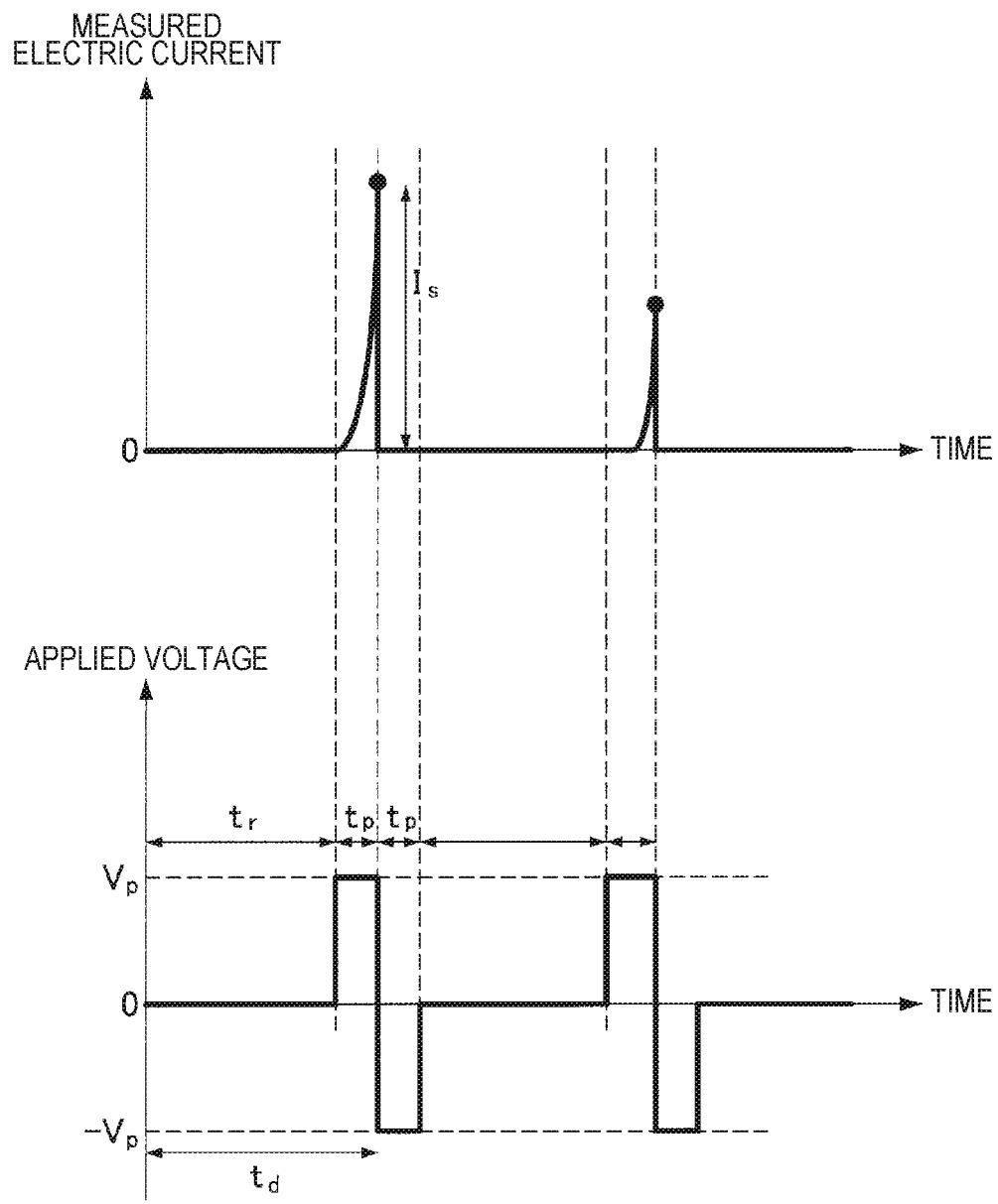
FIG. 4 is a graph diagram illustrating a relationship between a voltage applied to a pair of electrodes in the sensor portion and an electric current.

As shown in FIG. 4, first, the voltage control portion 151 applies a positive rectangular pulse voltage having a time width of $t_p$ (e.g., about 1 μsec) and a voltage of $V_p$ (e.g., about 100 mV) between the pair of electrodes 110 and 120 after the lapse of a time period $t_r$ (e.g., about 30 sec) required for the reaction between the enzyme to be detected and the electron generating capsule 140. By this operation, the ferrocyanide ion ($[Fe(CN)6]^{4-}$) contained in the electron transfer layer 130 is quickly drawn to the electrode at the anode side and converted to the ferricyanide ion ($[Fe(CN)6]^{3-}$) by releasing the electron. Thus, the detection portion 153 can obtain a measured electric current having the level of $I_s$ by virtue of the electron released to the electrode at the anode side.

Further, the voltage control portion 151 applies a negative pulse voltage symmetrical to the pulse voltage used for obtaining the measured electric current between the pair of electrodes 110 and 120. That is, the negative pulse voltage is a negative rectangular pulse voltage having a time width of $t_p$ (e.g., about 1 sec) and a voltage of $-V_p$ (e.g., about 100 mV). In the electron transfer layer 130, the ferricyanide ion is drawn to the anode side by the application of the positive rectangular pulse voltage, thus the application of the symmetrical negative rectangular pulse voltage can reverse the distribution of the ferricyanide ion in the electron transfer layer 130 to the original state.

In this manner, the enzyme sensor 1 can obtain the measured electric current in accordance with the amount of the enzyme to be detected using the detection portion 153 by applying the positive-negative rectangular pulse voltage having the period of $t_d$ ($t_d=t_r+2t_p$) between the pair of electrodes 110 and 120 of the sensor portion 100 using the voltage control portion 151.

Note that, as the pulse voltage applied by the voltage control portion 151, the pulse voltage with the short period as described above can be used without any problem. Specifically, the motion equations of the ferrocyanide ion (charge Q, mass M) during the application of voltage V are represented by the following equations 1 and 2, and an acceleration a of the ferrocyanide ion can be obtained by solving these equations. From this result, a time t taken for the ferrocyanide ion to move by a distance L to the electrode at the anode side is calculated using the equation 3 to be 1 μsec. Thus, as the pulse voltage applied by the voltage control portion 151, the pulse voltage with the short period as described above can be used without any problem. Note that μ represents an effective friction coefficient of the ferrocyanide ion moving in the electron transfer layer 130.

[Math. 1]

$$F = aM = \mu QE \quad \text{(equation 1)}$$

$$a = \frac{\mu QE}{M}, E = \frac{V}{L} \quad \text{(equation 2)}$$

$$L = \frac{1}{2}at^2 = \frac{\mu QV}{2ML} \rightarrow t = L \times \sqrt{\frac{2M}{\mu QV}} = 1[\mu s] \quad \text{(equation 3)}$$

In the above equations 1 to 3, each variable is assumed as follows.

V=0.4(V), Q=4e(C), M=212$M_p$, L=10(μm), μ=0.01

The alert portion 155 monitors the consumption of the substrate contained in the outer membrane 141 of the electron generating capsule 140 to determine the timing of replacing the enzyme sensor 1. The substrate contained in the outer membrane 141 of the electron generating capsule 140 is consumed by the reaction with the enzyme to be detected and thus decreases in accordance with the progress of the measurement by the enzyme sensor 1.

Thus, the enzyme sensor 1 needs to be replaced before the substrates contained in the outer membrane 141 of the electron generating capsule 140 are totally consumed in order to continue the measurement by the enzyme sensor 1. Specifically, the alert portion 155 determines the timing of replacing the enzyme sensor 1 on the basis of an integrated value of the measured electric current detected by the detection portion 153. Further, the alert portion 155 may notify the user that the enzyme sensor 1 needs to be replaced by display, audio, or a signal via the output portion 157.

Figure 5:
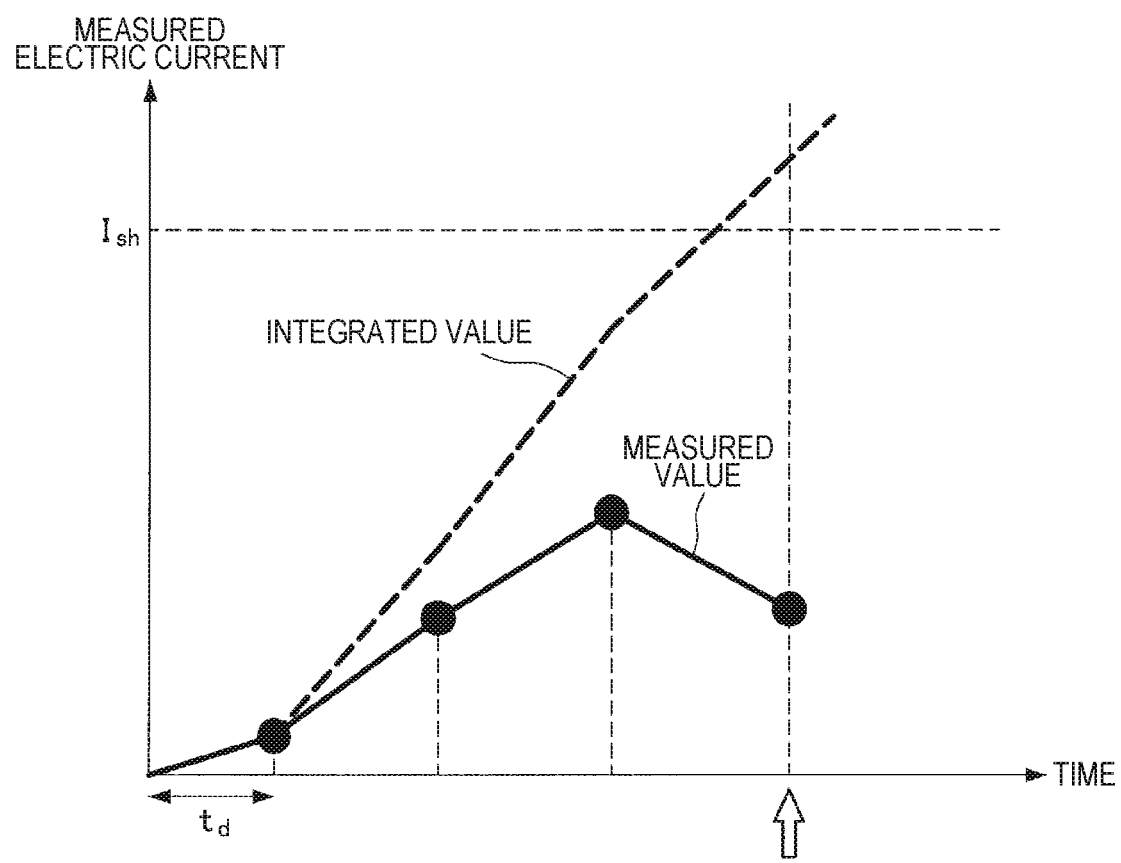
FIG. 5 is a graph diagram schematically illustrating a measured value and an integrated value of the electric current detected by a detection portion.

Here, a more specific description is given of the determination of the timing of replacing the enzyme sensor 1 by the alert portion 155 with reference to FIG. 5. FIG. 5 is a graph diagram schematically illustrating the measured value and the integrated value of the electric current detected by the detection portion 153.

As shown in FIG. 5, in a case where the detection portion 153 detects the electric current in accordance with the amount of the enzyme to be detected with the period of the time $t_d$, the alert portion 155 may integrate the electric current values measured by the detection portion 153 and notify the user that the enzyme sensor 1 needs to be replaced when the integrated value exceeds a threshold value $I_{sb}$.

The electric current value detected by the detection portion 153 is proportional to the amount of the electrolyte which has received the electron contained in the electron transfer layer 130, that is, the amount of the reaction between the enzyme to be detected and the electron generating capsule 140. Thus, the integrated value of the electric current measured by the detection portion 153 is proportional to the consumption of the substrate contained in the outer membrane 141 of the electron generating capsule 140. This allows the alert portion 155 to use the integrated value of the electric current measured by the detection portion 153 for the determination and thereby appropriately determine the timing of replacing the enzyme sensor 1 (the timing indicated by an arrow in the time axis in FIG. 4).

The output portion 157 outputs information on the basis of the electric current value detected by the detection portion 153 to the user or an external device. For example, the output portion 157 may output the information regarding an enzyme activity on the basis of the electric current value detected by the detection portion 153. Specifically, the output portion 157 may measure the electric current value corresponding to the enzyme amount at the normal time as a "standard electric current value", calculate the "enzyme activity" from the detected "measured electric current value" by performing the calculation on the basis of the following equation 4, and then output the calculated "enzyme activity".

[Math. 2]

$$\text{enzyme activity} = \frac{\text{measured electric current value} - \text{standard electric current value}}{\text{standard electric current value}} \quad \text{equation 4}$$

The amount of the secreted enzyme varies due to an individual difference in the living body, thus the level of the secreted amount of the enzyme in the living body of the subject can be more accurately represented by showing the enzyme activity as the increase and decrease in ratio relative to the enzyme amount in the normal time as described above.

In particular, in a case where the enzyme to be detected is amylase, the secreted amount of the amylase in the living body corresponds to the amount of the mental stress in the living body. Thus, for example, measuring the amylase activity using the enzyme sensor 1 makes it possible to estimate the degree of the mental stress in the subject wearing the enzyme sensor 1.

Note that the output portion 157 may output the electric current value detected by the detection portion 153 instead of the activity of the enzyme to be detected. In such a case, the calculation of the activity of the enzyme to be detected may be performed by the external device (e.g., an information processing device such as a smartphone or a personal computer) that acquires the outputted electric current value.

Further, the output portion 157 may output additional information other than the information related to the enzyme activity to the user or the external device. Specifically, the output portion 157 may output the notice issued by the alert portion 155 requesting the user to replace the enzyme sensor 1.

For example, the output portion 157 may output the information using a display device such as a liquid crystal display (LCD) device or an audio output device such as a speaker. Further, the output portion 157 may output the information to the external display device or audio output device via a wired or wireless local area network (LAN), Bluetooth (registered trademark), Wi-Fi (registered trademark), or the like.

According to the above configuration, the enzyme sensor 1 according to the present embodiment can measure the activity of the enzyme contained in the body fluid of the subject wearing the enzyme sensor 1 and the mental or physical state thereof in a non-invasive and real-time manner.

(1.3. Exemplary Operation of Enzyme Sensor)

Figure 6:
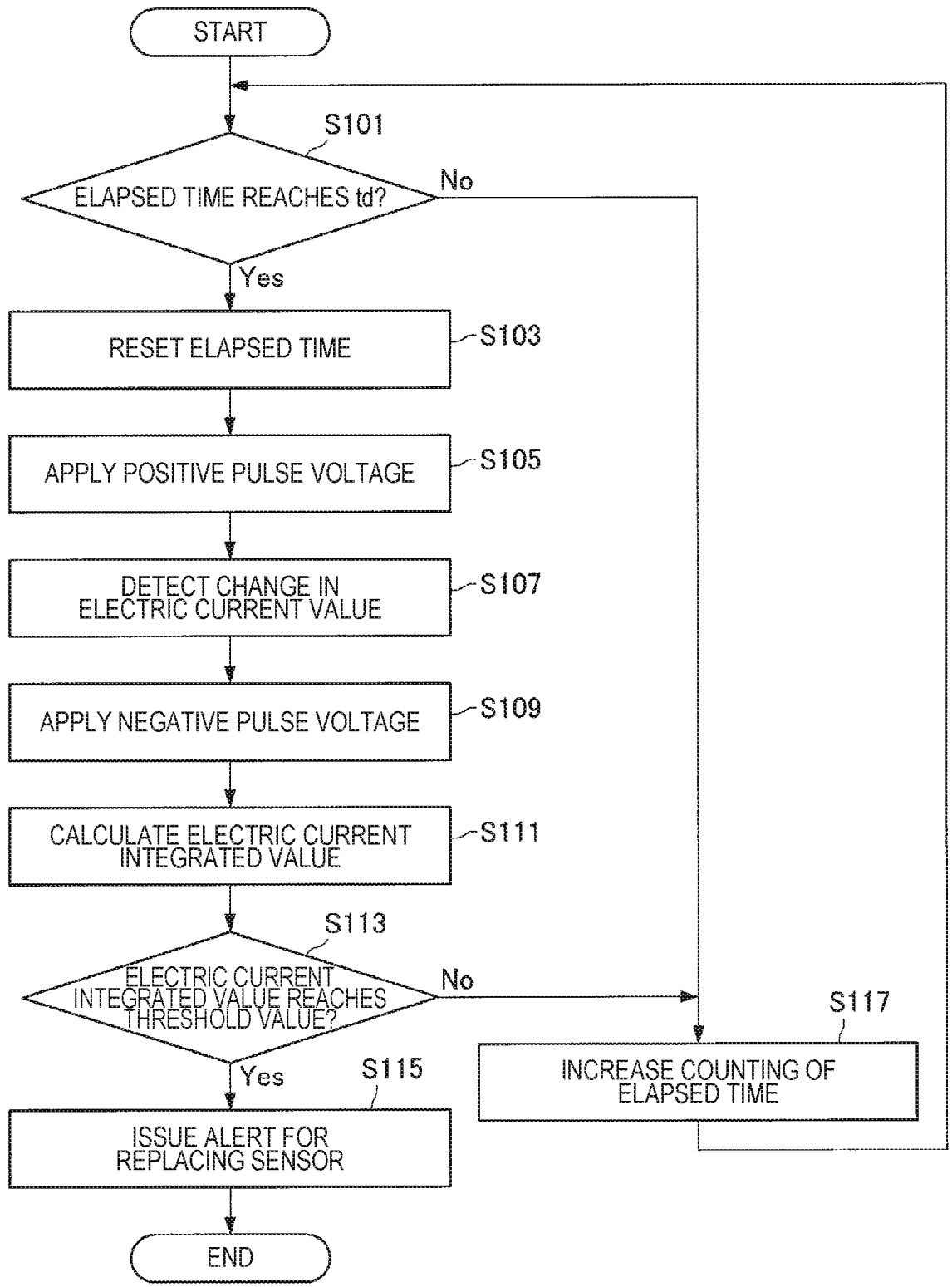
FIG. 6 is a flowchart showing an exemplary operation of the enzyme sensor according to the first embodiment.

Next, an exemplary operation of the enzyme sensor 1 according to the present embodiment will be described with reference to FIG. 6. FIG. 6 is a flowchart showing the exemplary operation of the enzyme sensor 1 according to the present embodiment.

As shown in FIG. 6. the enzyme sensor 1 first determines whether or not an elapsed time after starting the measurement has reached $t_d$ (S101). If the elapsed time has not reached $t_d$ (S101/No), the counting of the elapsed time increases (S117), and then it is determined again whether or not the elapsed time has reached $t_d$. On the other hand, if the elapsed time has reached $t_d$ (S101/Yes), the elapsed time is first reset (S103). Then, the voltage control portion 151 applies the positive pulse voltage between the pair of electrodes 110 and 120 of the sensor portion 100 (S105).

Next, the detection portion 153 detects a change in the electric current value on the basis of the amount of the electron accepted by the electrolyte contained in the electron transfer layer 130 of the sensor portion 100 (S107). Then, the voltage control portion 151 applies the negative pulse voltage between the pair of electrodes 110 and 120 of the sensor portion 100 (S109). By this operation, the electrolytes that have been drawn to the electrode at the anode side become uniformly distributed again in the electron transfer layer 130.

Subsequently, the alert portion 155 calculates the integrated value of the electric current (Sill). Further, the alert portion 155 determines whether or not the electric current integrated value has reached the threshold value (S113). If the electric current integrated value has not reached the threshold value (S113/No), the enzyme sensor 1 continues the measurement. Specifically, after the counting of the elapsed time is increased (S117), it is determined again whether or not the elapsed time has reached $t_d$ while the amount of the enzyme to be detected is measured. On the other hand, if the electric current integrated value has reached the threshold value (S113/Yes), the alert portion 155 issues an alert for notifying the replacement of the enzyme sensor 1 (S115). The alert issued by the alert portion 155 is notified to the wearer of the enzyme sensor 1 or the user thereof, for example, via the output portion 157.

With the above operations, the enzyme sensor 1 according to the present embodiment can measure the amount of the enzyme contained in the body fluid of the subject wearing the enzyme sensor 1. Further, the enzyme sensor 1 can notify the appropriate replacement timing of the enzyme sensor 1 to the user.

(1.4. Production Method of Enzyme Sensor)

Next, a production method of the enzyme sensor 1 according to the present embodiment will be described with reference to FIGS. 7A, 7B, 7C, 7D, 7E, 7F, 8A, 8B, and 8C. FIGS. 7A, 7B, 7C, 7D, 7E, and 7F are perspective views illustrating each production step of the enzyme sensor 1 according to the present embodiment.

Figure 7A:
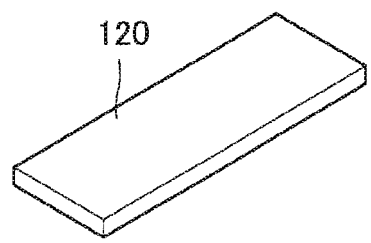
FIG. 7A is a perspective view illustrating one production step of the enzyme sensor according to the first embodiment.

As shown in FIG. 7A, first, the electrode 120 is formed by sputtering or the like on a substrate (not illustrated) in which a logic circuit configured using a via, a transistor, and the like is formed. The electrode 120 can be formed of, for example, silver (Ag) or carbon (C). Further, the electrode 120 may be formed by a film forming process hardly causing an interface defect so that the electrode 120 can detect the output of the electric current of about several hundred μA to 1 mA.

Figure 7B:
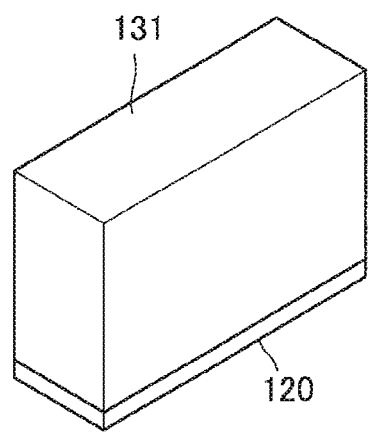
FIG. 7B is a perspective view illustrating one production step of the enzyme sensor according to the first embodiment.

Subsequently, as shown in FIG. 7B, an electron transfer material layer 131 is formed on the electrode 120. The electron transfer material layer 131 can be formed, for example, by applying a potassium ferricyanide solution on the electrode 120 and then gelatinating the applied solution.

Figure 7C:
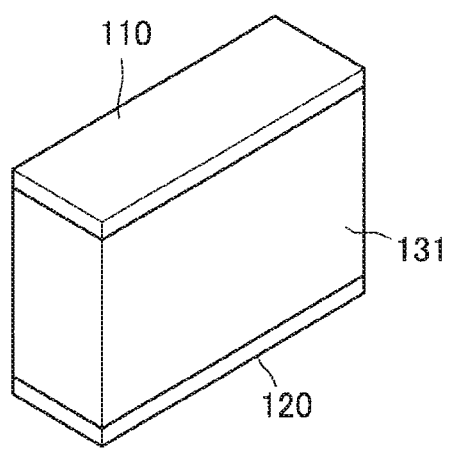
FIG. 7C is a perspective view illustrating one production step of the enzyme sensor according to the first embodiment.

Next, as shown in FIG. 7C, the electrode 110 is formed on the electron transfer material layer 131 by sputtering or the like. The electrode 110 can be formed of, for example, a similar material used for the electrode 120.

Figure 7D:
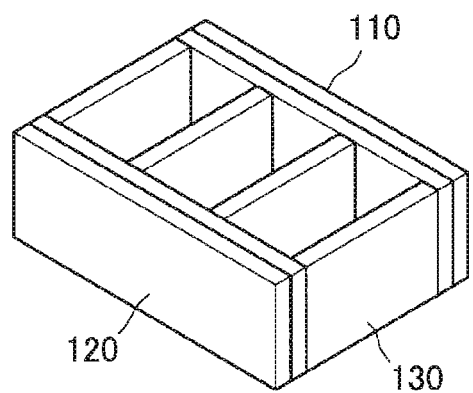
FIG. 7D is a perspective view illustrating one production step of the enzyme sensor according to the first embodiment.

Subsequently, as shown in FIG. 7D, a plurality of the concave structures is formed on one surface of the electron transfer material layer 131 not being held between the electrodes 110 and 120 by using a nanoimprinting method or the like, resulting in the formation of the electron transfer layer 130.

Figure 7E:
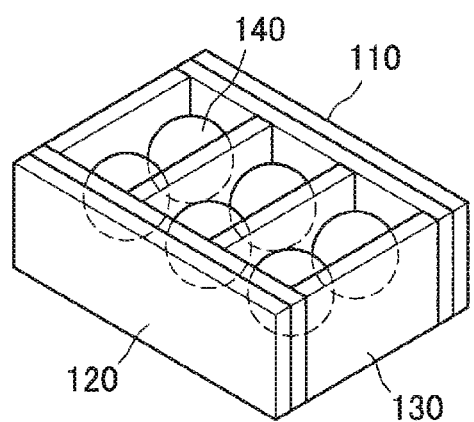
FIG. 7E is a perspective view illustrating one production step of the enzyme sensor according to the first embodiment.

Next, as shown in FIG. 7E, a plurality of the electron generating capsules 140 is arranged inside the concave structure of the electron transfer layer 130. The method for forming the electron generating capsule 140 will be described below with reference to FIGS. 8A, 8B, and 8C.

Figure 7F:
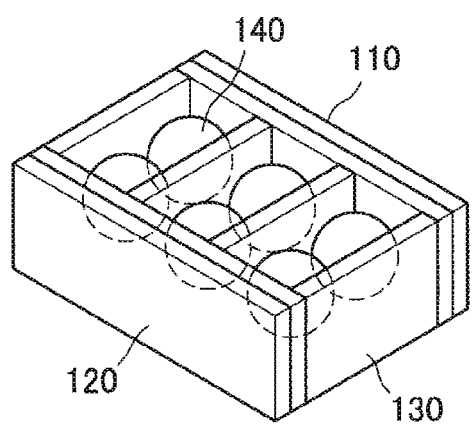
FIG. 7F is a perspective view illustrating one production step of the enzyme sensor according to the first embodiment.

Further, as shown in FIG. 7F, a solution constituting the electron transfer layer 130 is poured inside the concave structure of the electron transfer layer 130 so as to immerse the plurality of the electron generating capsules 140 up to approximately the half of the depth of them. Further, the solution poured inside the concave structure of the electron transfer layer 130 is gelatinized. As the solution constituting the electron transfer layer 130, for example, a potassium ferricyanide solution can be used.

Figure 8A:
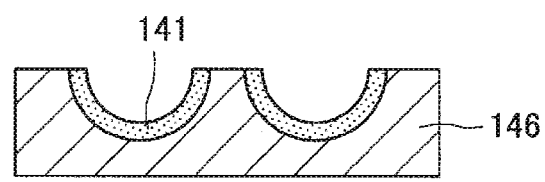
FIG. 8A is a sectional view illustrating one production step of an electron generating capsule used in the enzyme sensor according to the first embodiment.
Figure 8B:
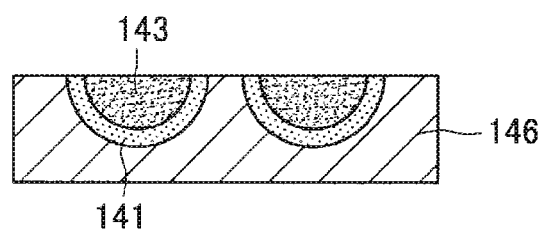
FIG. 8B is a sectional view illustrating one production step of an electron generating capsule used in the enzyme sensor according to the first embodiment.
Figure 8C:
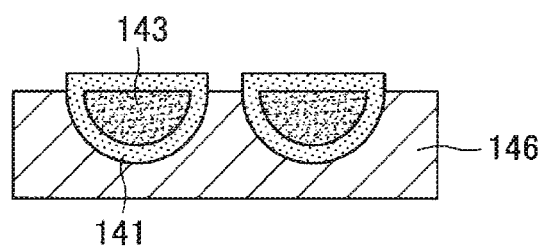
FIG. 8C is a sectional view illustrating one production step of an electron generating capsule used in the enzyme sensor according to the first embodiment.

Here, the production method of the electron generating capsules 140 used in the enzyme sensor 1 will be described reference to FIGS. 8A, 8B, and 8C. FIGS. 8A, 8B, and 8C are sectional views illustrating each production step of the electron generating capsule 140 used in the enzyme sensor 1.

As shown in FIG. 8A, for forming the electron generating capsules 140, a material of the outer membrane 141 is first applied to a mold 146 having a hemispherical shape. Starch can be used as the material of the outer membrane 141. When water is added, the starch can be reversibly switched between a gelatinized state and a retrograded state by heating or cooling, thus the starch can be applied to the mold 146 by appropriately adjusting the state of the starch and thereby optimizing its viscosity.

Next, as shown in FIG. 8B, the content liquid 143 is applied in the mold 146 in which the material of the outer membrane 141 has been applied, and dried. The content liquid 143 may be, for example, a water-dispersion solution in which glucose oxidase and maltase are stabilized by PMEH. Glucose oxidase and maltase can be stably immobilized by PMEH inside the electron generating capsules 140.

Subsequently, as shown in FIG. 8C, the material of the outer membrane 141 is further applied on the mold 146 in which the content liquid 143 has been applied to seal the content liquid 143 inside the outer membrane 141. Further, the electron generating capsules 140 having a hemispherical shape formed in FIG. 8C can be taken out from the molds 146 and bonded to each other through their flat surfaces to form the electron generating capsule 140 having a substantially spherical shape. Note that, in a case where the electron generating capsule 140 does not need to be formed in a substantially spherical shape, the product formed in the hemispherical shape in FIG. 8C can be used as it is as the electron generating capsule 140.

The enzyme sensor 1 according to the present embodiment can be produced by the steps described above. Note that the above production method is only an example and the production method of the enzyme sensor 1 according to the present embodiment is not limited to the above example.

2. Second Embodiment

Figure 9:
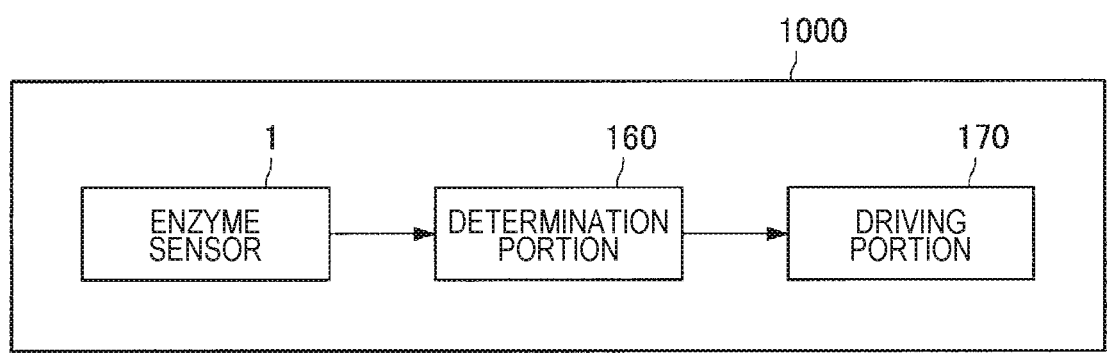
FIG. 9 is a block diagram explaining a configuration of an electronic device according to a second embodiment of the present disclosure.

Next, an electronic device 1000 according to a second embodiment of the present disclosure will be described with reference to FIG. 9. FIG. 9 is a block diagram explaining a configuration of the electronic device 1000 according to the second embodiment of the present disclosure.

As shown in FIG. 9, the electronic device 1000 includes the enzyme sensor 1 according to the first embodiment of the present disclosure, a determination portion 160, and a driving portion 170. That is, the electronic device 1000 according to the second embodiment of the present disclosure determines the state of the subject wearing the enzyme sensor 1 on the basis of the amount of the enzyme to be detected obtained from the enzyme sensor 1 according to the first embodiment of the present disclosure and performs driving corresponding to the state of the subject thus determined. Note that the enzyme sensor 1 has been described in the first embodiment and the repeated description thereof is omitted here.

The determination portion 160 is a determination circuit or a program that determines the state of the subject wearing the enzyme sensor 1 on the basis of a measurement result of the enzyme sensor 1. The determination portion 160 may determine, for example, the presence or absence of a disease of the subject wearing the enzyme sensor 1 or a degree of the mental stress of the subject wearing the enzyme sensor 1 on the basis of the enzyme activity.

The driving portion 170 is a driving circuit or a program that performs an operation corresponding to the state of the subject wearing the enzyme sensor 1 on the basis of the determination of the determination portion 160. Specifically, the driving portion 170 may perform the operation so as to restore the state of the subject wearing the enzyme sensor 1 to the normal state or lead the state of the subject wearing the enzyme sensor 1 to the specific state. An output of the driving portion 170 may be, for example, display of text or image, emission of light, playback of audio, music or the like, a release of fragrance (aroma), or a mechanical operation of robot or the like.

Such an electronic device 1000 can be widely applicable to a medical treatment, a health care, entertainment, security, a pet or an animal, robotics, a storefront sale, a general affair, and the like.

For example, according to the electronic device 1000, it becomes possible to objectively display the effect of an antidepressant over time by displaying the degree of pain of a patient sedated by anesthesia on the basis of the degree of the stress. Further, according to the electronic device 1000, it becomes possible to lead the subject to a stress reduction state by selecting or delivering a music obtained by pattern matching for reducing the stress degree, or by releasing fragrance, on the basis of the degree of the stress of the subject. Further, according to the electronic device 1000, it becomes possible to switch a difficulty level of a game, a scene of a movie or amusement, or the like on the basis of the degree of the stress of the subject.

Further, according to the electronic device 1000, it becomes possible to automatically set a safety level of a vehicle or a factory device on the basis of the state of the subject. Further, according to the electronic device 1000, it becomes possible to allow an owner to share a pet's emotion by emitting light with a color on the basis of the mental state of the pet or the like. Further, according to the electronic device 1000, it becomes possible to control an operation of a robot or the like so as to mitigate the mental state of the subject on the basis of the mental state thereof. Further, according to the electronic device 1000, it becomes possible to display a recommended product in accordance with the mental state of a customer by grasping the mental state thereof. Further, according to the electronic device 1000, it becomes possible to facilitate the efficient work performance by displaying the mental state of an employee using a light-emitting device or the like.

Note that the determination portion 160 and the driving portion 170 may be achieved, for example, by the cooperation of a hardware such as a CPU, a RAM, and a ROM and a software that controls the operation of each configuration. Further, the determination portion 160 and the driving portion 170 may be an information processing device formed separately from the enzyme sensor 1, such as a smartphone or a personal computer.

3. Specific Examples

Next, a specific example corresponding to each embodiment of the present disclosure will be described with reference to FIG. 10 to FIG. 18.

The enzyme sensor 1 according to the first embodiment of the present disclosure can detect various enzymes by changing the substrate contained in the outer membrane 141 of the electron generating capsules 140 and the enzyme contained in the content liquid 143. In the following description, the enzyme sensor detecting amylase as the enzyme to be detected is shown as a first specific example, the enzyme sensor detecting lipase as the enzyme to be detected is shown as a second specific example, and the enzyme sensor detecting sucrase as the enzyme to be detected is shown as a third specific example.

Note that, in the first to third specific examples, each configuration with the same name as that described in the first embodiment has substantially the same function or the like, thus the description thereof will be omitted below.

(3.1. First Specific Example)

Figure 10:
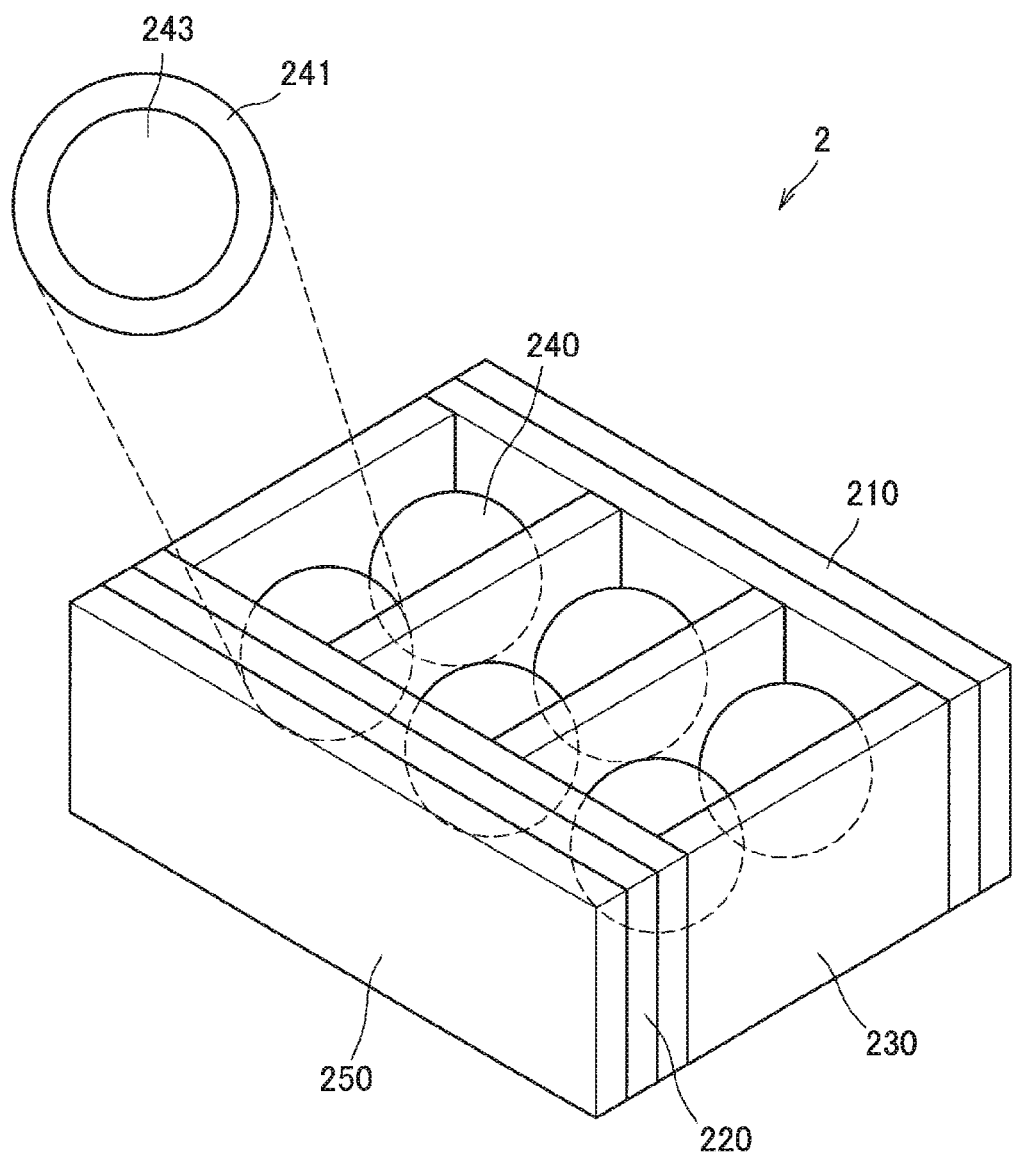
FIG. 10 is a perspective view illustrating a structure of the enzyme sensor according to a first specific example.
Figure 11:
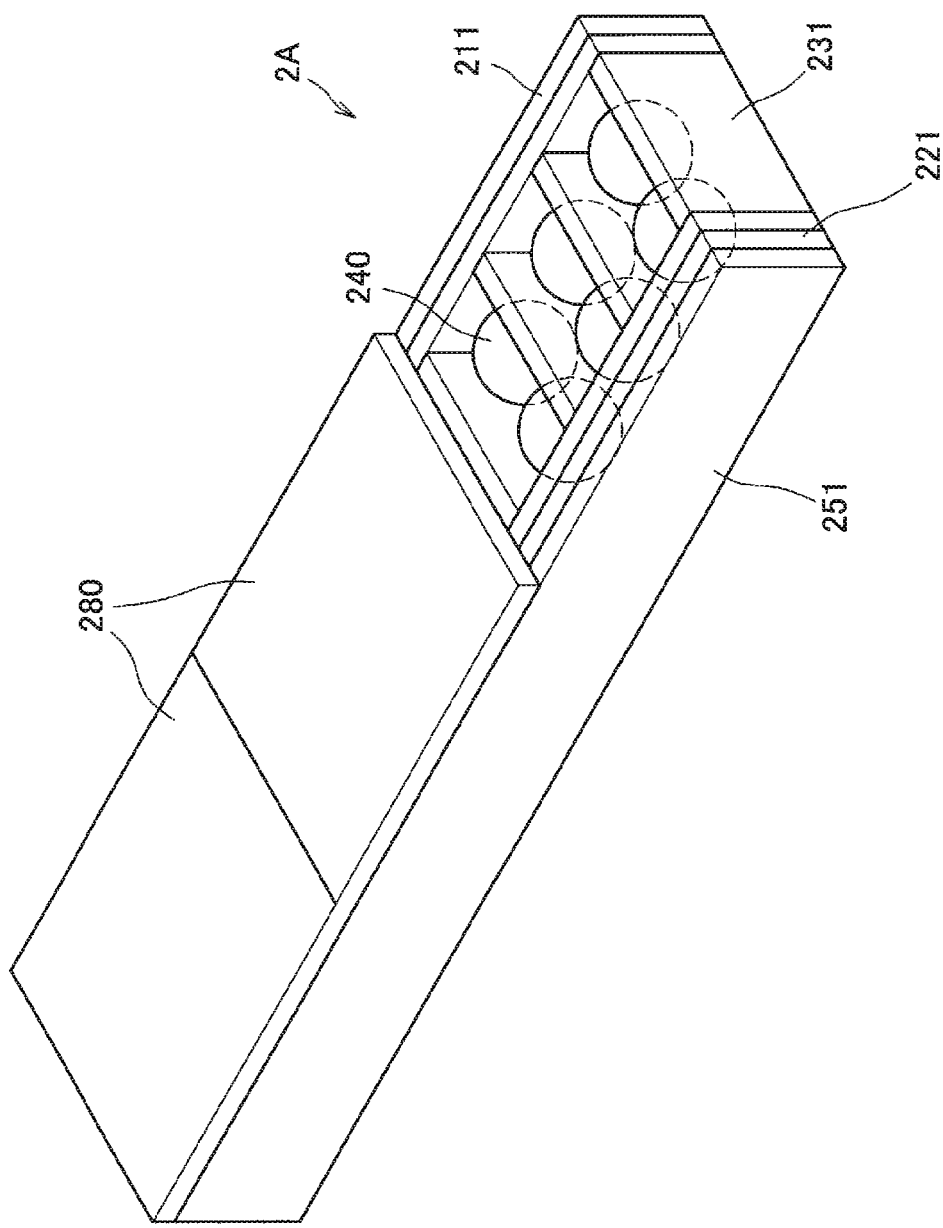
FIG. 11 is a perspective view illustrating a modification example of the enzyme sensor according to the first specific example.

First, an enzyme sensor 2 according to the first specific example will be described with reference to FIG. 10 to FIG. 15. FIG. 10 is a perspective view illustrating a structure of the enzyme sensor 2 according to the first specific example. FIG. 11 is a perspective view illustrating a modification example of the enzyme sensor 2 according to the first specific example.

As shown in FIG. 10, the enzyme sensor 2 according to the first specific example includes a logic portion 250, a pair of electrodes 210 and 220, an electron transfer layer 230, and an electron generating capsule 240. The enzyme sensor 2 according to the first specific example is, for example, a sensor that estimates the degree of the mental stress of the subject wearing the enzyme sensor 2 by detecting the amount of amylase in the saliva.

The logic portion 250 is arranged so as to be electrically connected to the anode side of the pair of electrodes 210 and 220. The logic portion 250 may be, for example, a silicon substrate in which a via, a transistor, and the like are formed.

The pair of electrodes 210 and 220 may be parallel flat plates holding the electron transfer layer 230 therebetween and formed of, for example, silver (Ag) or the like. The longitudinal length of the pair of electrodes 210 and 220 may be, for example, about 500 µm.

The electron transfer layer 230 is a layer formed by gelatinating a solution containing an electrolyte capable of accepting the electron and held between the pair of electrodes 210 and 220. Further, three concave structures may be formed on one surface of the electron transfer layer 230 not being held between the pair of electrodes 210 and 220. The electron transfer layer 230 may be formed of, for example, a gelatinized potassium ferricyanide solution.

The electron generating capsule 240 is formed in, for example, a substantially spherical shape having the diameter of 100 µm and has a structure in which a content liquid 243 containing glucose oxidase, maltase, and PMEH is enclosed by an outer membrane 241 formed of starch. For example, two electron generating capsules 240 may be retained inside each of the three concave structures of the electron transfer layer 230.

Further, a reaction region including the concave structure of the electron transfer layer 230 may be covered with a positive ion exchange membrane. Using the positive ion exchange membrane can prevent the elution of the ferricyanide ion contained in the electron transfer layer 230 by the water content of the saliva containing the amylase or the like.

In such an enzyme sensor 2, the logic portion 250 can read the electric current value corresponding to the amount of the amylase by applying a positive-negative pulse voltage of 400 mV for about 1 second between the pair of electrodes 210 and 220. Note that the enzyme sensor 2 may detect the amount of the amylase in the period of 32 seconds by allowing about 30 seconds for the amylase enzymatic reaction.

Next, a modification example of the enzyme sensor 2 according to the first specific example will be described with reference to FIG. 11. The modification example of the enzyme sensor 2 according to the first specific example represents an example in which a plurality of the reaction regions with the amylase is arranged in the electron transfer layer 231 and the reaction regions reacting with the amylase in the electron transfer layer 231 are switched by a mechanical control.

As shown in FIG. 11, in an enzyme sensor 2A according to the modification example, a pair of electrodes 211 and 221 and the electron transfer layer 231 are arranged to be extended in one direction and a part of an opening of the plurality of concave structures arranged in the electron transfer layer 231 is covered with a shielding plate 280.

The shielding plate 280 separates the electron generating capsules 240 retained in the concave structure of the electron transfer layer 231 from the saliva containing the amylase. Further, the shielding plate 280 is arranged movable to open the opening of the concave structure of the electron transfer layer 231, which has been shielded by the shielding plate 280, in accordance with the consumption of the starch contained in the outer membrane of the electron generating capsule 240. For example, a logic portion 251, which includes a micro electro mechanical system (MEMS) element for controlling the shielding plate 280, may control the opening and closing of the shielding plate 280 in accordance with the consumption (i.e., the integrated value of the measured electric current) of the starch contained in the outer membrane of the electron generating capsule 240.

In such a configuration, the enzyme sensor 2A can continue the measurement by moving the shielding plate 280 to open the new reaction region without replacing the enzyme sensor 2A itself even when the starch contained in the outer membrane of the electron generating capsule 240 is consumed.

Note that the shielding plate 280 may be controlled so as to move on a plane along the pair of electrodes 211 and 221. In such a case, the area of the reaction region contactable with the saliva containing the amylase can be always kept constant.

The material of the shielding plate 280 is not particularly limited, and, for example, any durable material with less corrosion or the like can be used. For example, the shielding plate 280 may be formed of metal or a resin.

Figure 12:
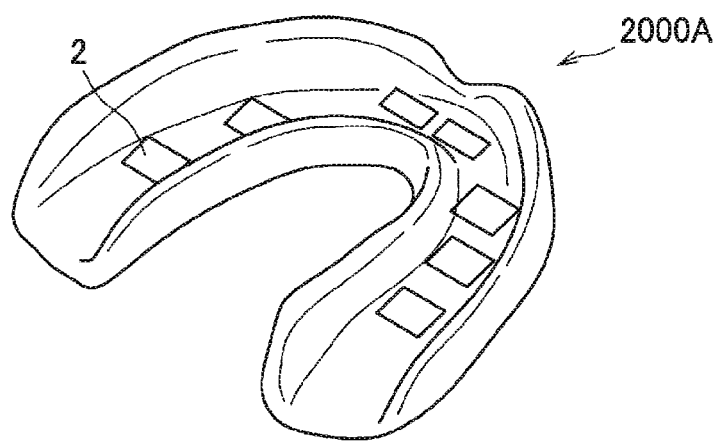
FIG. 12 is a perspective view illustrating a wearing mode of the enzyme sensor according to the first specific example.
Figure 13:
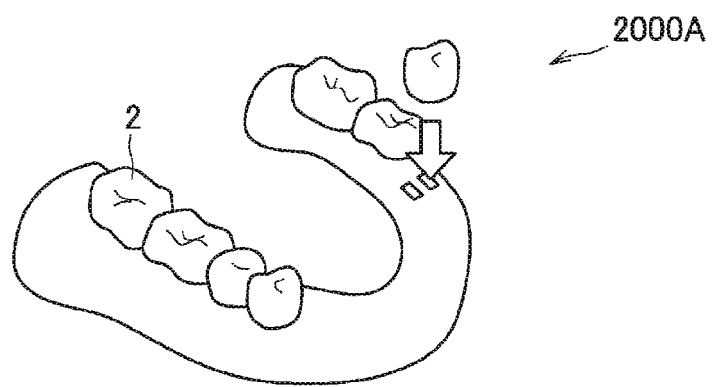
FIG. 13 is a perspective view illustrating another wearing mode of the enzyme sensor according to the first specific example.
Figure 14:
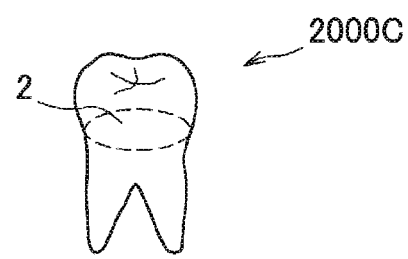
FIG. 14 is a perspective view illustrating another wearing mode of the enzyme sensor according to the first specific example.

Next, a mode of wearing the aforementioned enzyme sensor 2 will be described with reference to FIG. 12 to FIG. 14. FIG. 12 to FIG. 14 are perspective views illustrating the modes of wearing the enzyme sensor 2.

The enzyme sensor 2 according to the first specific example 1 is a sensor that detects the amount of the amylase contained in the saliva in the oral cavity and thus implemented in the mode wearable in the oral cavity.

For example, as shown in FIG. 12, the enzyme sensor 2 may be implemented in a mouthpiece 2000A. Further, the mouthpiece 2000A may be implemented with other various modules such as an acceleration sensor, a global navigation satellite system (GNSS) sensor, a radio frequency (RF) module, a power generation module, and a power storage module. Note that an orifice (i.e., an opening) may be formed in the mouthpiece 2000A so as to allow the contact between the enzyme sensor 2 and the saliva.

Further, for example, as shown in FIG. 13, the enzyme sensor 2 may be implemented in a denture 2000B. Note that the denture 2000B may be similarly implemented with the various modules such as the acceleration sensor, the GNSS sensor, the RF module, the power generation module, and the power storage module. When the various modules are implemented in the denture 2000B, the various modules are each implemented in a separate tooth so that the module can be easily replaced by replacing the corresponding tooth. Note that an orifice may be similarly formed in the denture 2000B so as to allow the contact between the enzyme sensor 2 and the saliva.

Further, for example, as shown in FIG. 14, the enzyme sensor 2 may be implemented in a crown 2000C. Note that an orifice may be similarly formed in the crown 2000C so as to allow the contact between the enzyme sensor 2 and the saliva.

Figure 15:
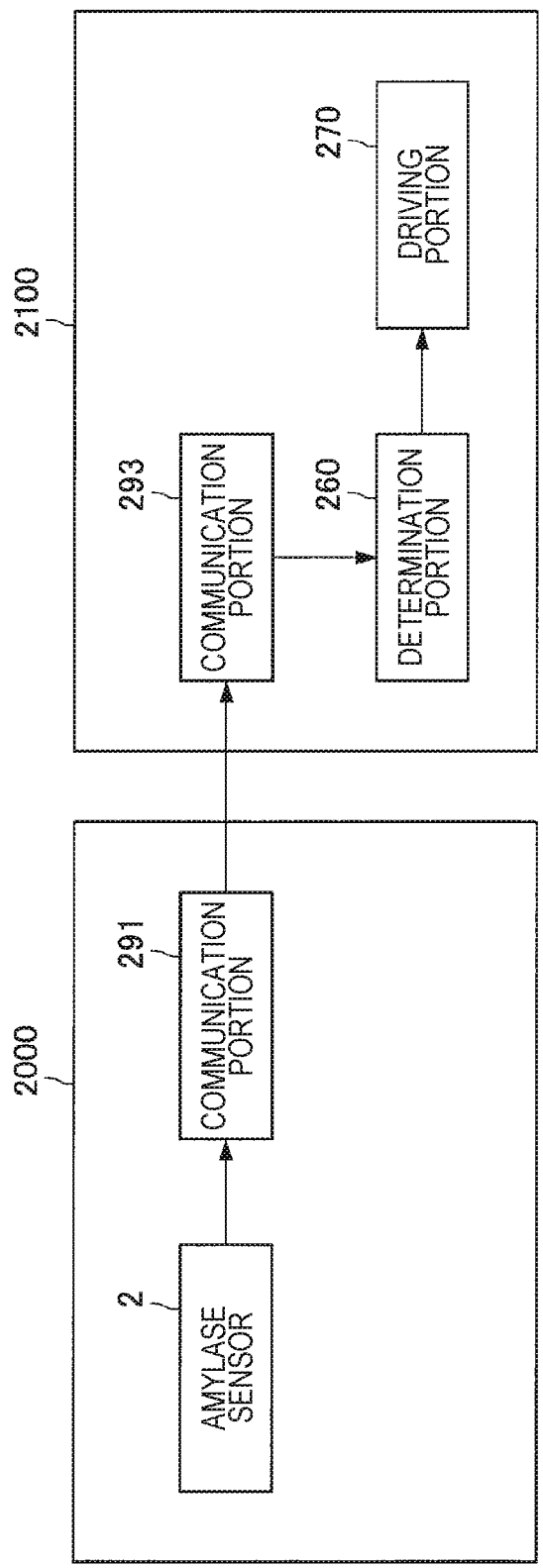
FIG. 15 is a block diagram explaining a configuration of the electronic device according to the first specific example.

Further, an electronic device 2100 that operates on the basis of a measurement result of the enzyme sensor 2 (i.e., the amylase sensor) according to the first specific example will be described with reference to FIG. 15. FIG. 15 is a block diagram explaining a configuration of the electronic device 2100 according to the first specific example.

As shown in FIG. 15, the electronic device 2100 according to the first specific example includes a communication portion 293, a determination portion 260, and a driving portion 270. Further, the electronic device 2100 performs determination and driving on the basis of information related to the amount of the amylase received from a sensor 2000 including the enzyme sensor 2 and a communication portion 291.

The sensor 2000 is worn, for example, in the oral cavity so as to be contacted with the saliva containing the amylase. Thus, the sensor 2000 preferably performs the transmission and reception of the information with the electronic device 2100 through wireless communication. The communication portion 291 and the communication portion 293 may be, for example, an antenna and a communication circuit compatible with Bluetooth (registered trademark) or Wi-Fi (registered trademark).

For example, the electronic device 2100 may be an electronic device such as a game machine that realizes virtual reality (VR). Specifically, the sensor 2000 detects the amount of the amylase corresponding to the user's mental stress by the enzyme sensor 2 and transmits the detected amylase amount to the electronic device 2100. The electronic device 2100 calculates the activity of the amylase from the received amylase amount and determines a response corresponding to the amylase activity using the determination portion 260. Further, the response determined by the determination portion 260 is outputted by the driving portion 270. For example, the response determined by the determination portion 260 may be outputted as a behavior or action of a human figure displayed on the VR by the driving portion 270.

By repeating these operations, the electronic device 2100 can lead the user to the specific mental state unconsciously. For example, the electronic device 2100 may lead the user's mental state to the relaxed state by interaction between the user and the human figure on the VR. Further, the electronic device 2100 may lead the user's mental state in a direction of increasing the fear by responses between the user and the human figure on the VR.

Note that, the output by the driving portion 270 of the electronic device 2100 is not limited to the display on the VR described above, and various outputs that can be perceived by the user can be used. For example, the output by the driving portion 270 may be one of text display, audio playback, music performance, image display, a light emitting operation, a release of a compound, or a mechanical operation. Further, the electronic device 2100 may be electronic devices in various modes such as a smartphone, a personal computer, a wearable terminal, or a television device.

(3.2. Second Specific Example)

Figure 16:
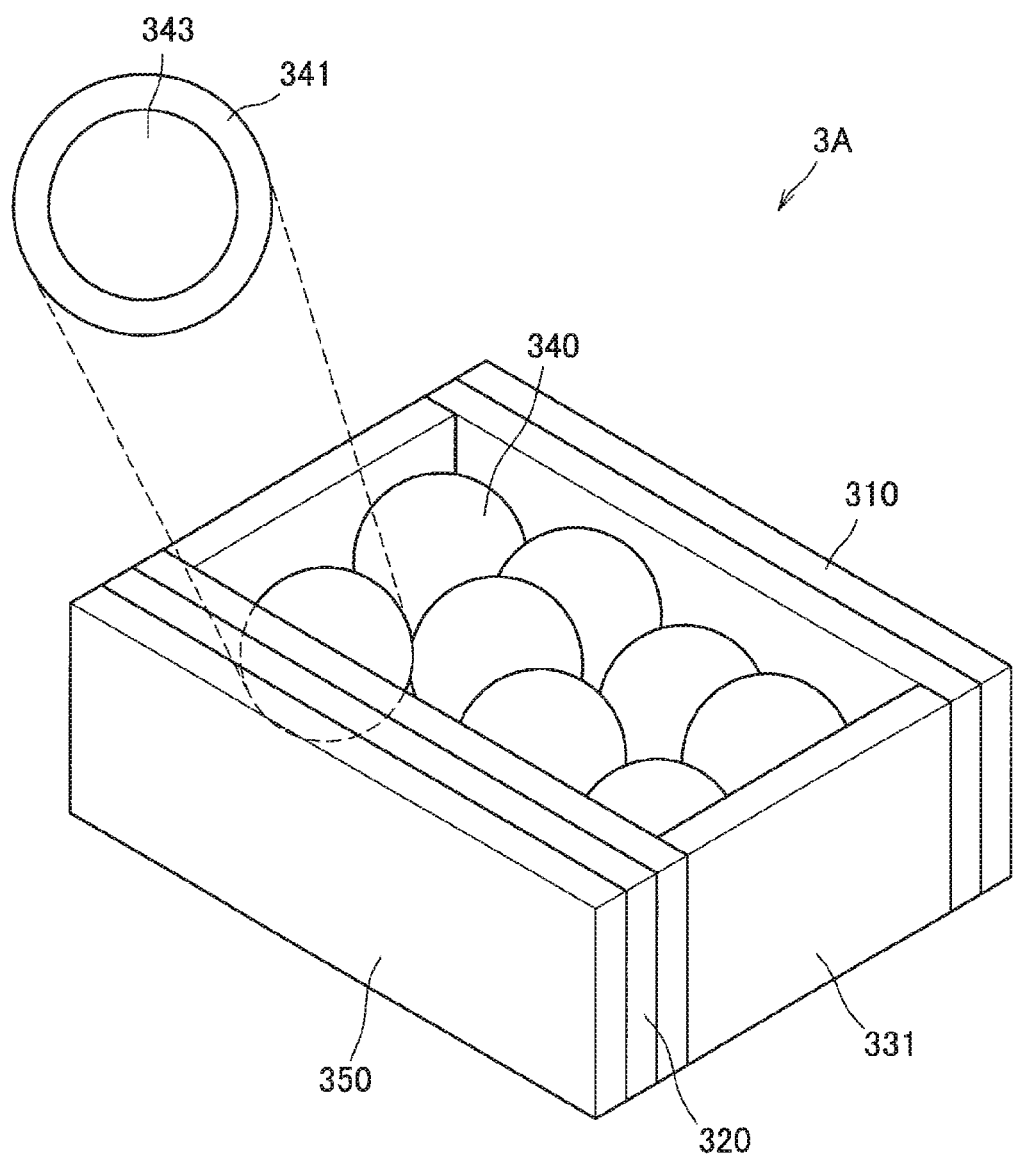
FIG. 16 is a perspective view illustrating an exemplary structure of the enzyme sensor according to a second specific example.
Figure 17:
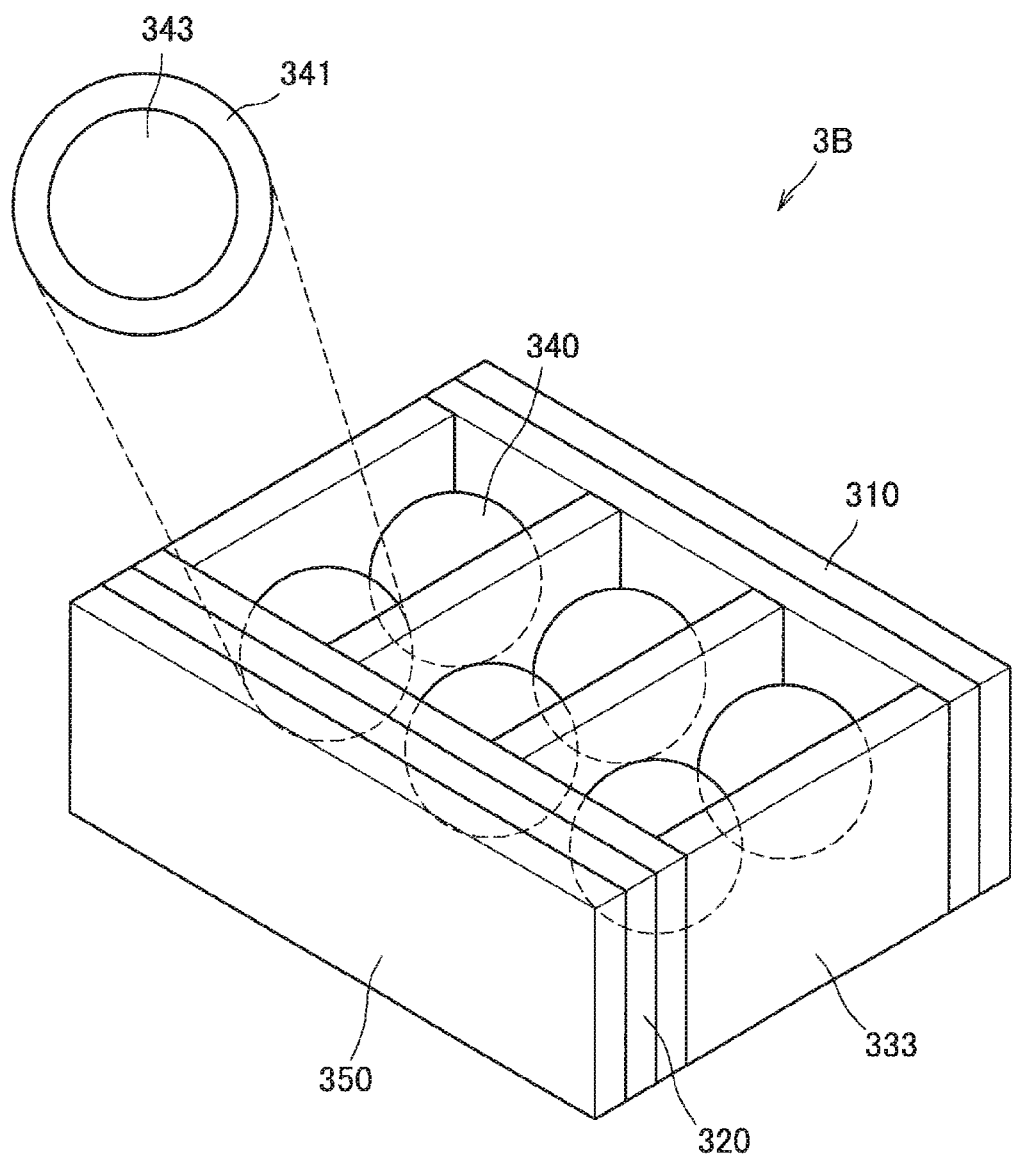
FIG. 17 is a perspective view illustrating another exemplary structure of the enzyme sensor according to the second specific example.

Next, an enzyme sensor according to a second specific example will be described with reference to FIG. 16 and FIG. 17. FIG. 16 is a perspective view illustrating an exemplary structure of the enzyme sensor according to the second specific example and FIG. 17 is a perspective view illustrating another exemplary structure of the enzyme sensor according to the second specific example.

As shown in FIG. 16, an enzyme sensor 3A according to the second specific example includes a logic portion 350, a pair of electrodes 310 and 320, an electron transfer layer 331, and an electron generating capsule 340. The enzyme sensor 3A according to the second specific example is, for example, a sensor that predicts the presence or absence of a disease of the pancreas of the subject wearing the enzyme sensor 3A by detecting the amount of lipase in the saliva.

The logic portion 350 is arranged so as to be electrically connected to the anode side of the pair of electrodes 310 and 320. The logic portion 350 may be, for example, a silicon substrate in which a via, a transistor, and the like are formed.

The pair of electrodes 310 and 320 are parallel flat plates holding the electron transfer layer 330 therebetween and may be formed of, for example, carbon (C) or the like. The longitudinal length of the pair of electrodes 310 and 320 may be, for example, about 1,000 μm.

The electron transfer layer 331 is a layer formed by gelatinating a solution containing an electrolyte capable of accepting the electron and held between the pair of electrodes 310 and 320. Further, a single concave structure may be formed on one surface of the electron transfer layer 331 not being held between the pair of electrodes 310 and 320. The electron transfer layer 331 may be formed of, for example, a gelatinized potassium ferricyanide solution.

The electron generating capsule 340 is formed in, for example, a substantially spherical shape having the diameter of 200 μm and has a structure in which a content liquid 343 containing acyl-CoA dehydrogenase, flavin adenine dinucleotide (FAD), fatty acid thiokinase, and PMEH is enclosed by an outer membrane 341 formed of a neutral fat (i.e., triglyceride). For example, a plurality of the electron generating capsules 340 may be retained inside the concave structure of the electron transfer layer 331.

Further, a reaction region including the concave structure of the electron transfer layer 331 may be covered with a positive ion exchange membrane. Using the positive ion exchange membrane can prevent the elution of the ferricyanide ion contained in the electron transfer layer 331 by the water content of the saliva containing the lipase or the like.

In such an enzyme sensor 3A, first, the lipase to be detected and the neutral fat contained in the outer membrane 341 are reacted to produce a fatty acid. Next, the fatty acid thiokinase, which is contained in the content liquid 343 and oozes to the outer membrane 341 by the difference of the osmotic pressure, and the fatty acid are reacted to produce amyl-CoA. Subsequently, the acyl-CoA dehydrogenase and the FAD contained in the content liquid 343 and the amyl-CoA are reacted to take out the electron from the amyl-CoA. Further, the electron taken out from the amyl-CoA is accepted by the ferricyanide ion or the like contained in the electron transfer layer 331. In this manner, the ferricyanide ion is converted to the ferrocyanide ion.

The above reactions are represented by the following chemical formulas 3 and 4.

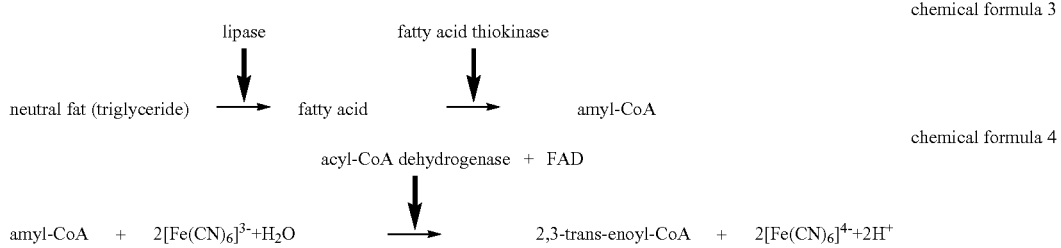

[Chem. 2]

chemical formula 3 neutral fat (triglyceride) $\xrightarrow{\text{lipase}}$ fatty acid $\xrightarrow{\text{fatty acid thiokinase}}$ amyl-CoA chemical formula 4 amyl-CoA + $2[Fe(CN)_6]^{3-}$ + $H_2O$ $\xrightarrow{\text{acyl-CoA dehydrogenase + FAD}}$ 2,3-trans-enoyl-CoA + $2[Fe(CN)_6]^{4-}$ + $2H^+$ Thus, in the enzyme sensor 3A, the logic portion 350 can read the electric current value corresponding to the amount of the lipase by applying a positive-negative pulse voltage of 400 mV for about 1 second between the pair of electrodes 310 and 320. Note that the enzyme sensor 3A may detect the amount of the lipase in the period of 32 seconds by allowing about 30 seconds for the lipase enzymatic reaction.

Further, the enzyme sensor according to the second specific example can adopt a structure other than the ones described above. For example, as shown in FIG. 17, the enzyme sensor 3B according to the second specific example may include an electron transfer layer 333 in which a plurality of the concave structures is arranged. In the enzyme sensor 3B shown in FIG. 17, the electron transfer layer 333 includes three concave structures, each of which retains two electron generating capsules 340. The enzyme sensor 3B in such a configuration can also detect the amount of the lipase.

That is, the number of the concave structures arranged in the electron transfer layer and the number of the electron generating capsules are not particularly limited and any number capable of appropriately detecting the enzyme to be detected can be selected.

(3.3. Third Specific Example)

Figure 18:
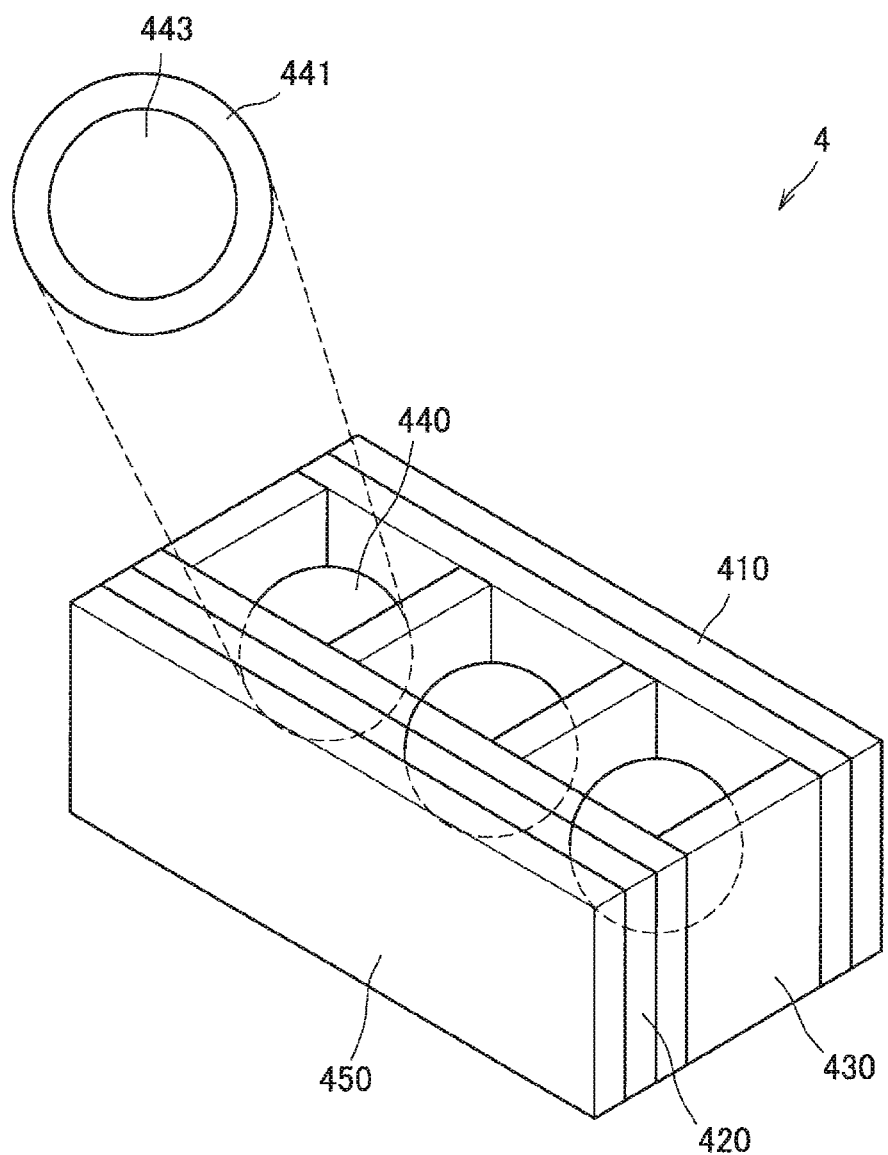
FIG. 18 is a perspective view illustrating an exemplary structure of the enzyme sensor according to a third specific example.

Next, an enzyme sensor 4 according to a third specific example will be described with reference to FIG. 18. FIG. 18 is a perspective view illustrating an exemplary structure of the enzyme sensor 4 according to the third specific example.

As shown in FIG. 18, the enzyme sensor 4 according to the third specific example includes a logic portion 450, a pair of electrodes 410 and 420, an electron transfer layer 430, and an electron generating capsule 440. The enzyme sensor 4 according to the third specific example is, for example, a sensor that predicts the state of the small intestine and the presence or absence of a disease of the small intestine of the subject wearing the enzyme sensor 4 by detecting the amount of sucrase in the intestinal juice.

The logic portion 450 is arranged so as to be electrically connected to the anode side of the pair of electrodes 410 and 420. The logic portion 450 may be, for example, a silicon substrate in which a via, a transistor, and the like are formed.

The pair of electrodes 410 and 420 are parallel flat plates holding the electron transfer layer 430 therebetween and may be formed of, for example, silver (Ag) or the like. The longitudinal length of the pair of electrodes 410 and 420 may be, for example, about 1,000 μm.

The electron transfer layer 430 is a layer formed by gelatinating a solution containing an electrolyte capable of accepting the electron and held between the pair of electrodes 410 and 420. Further, three concave structures may be formed on one surface of the electron transfer layer 430 not being held between the pair of electrodes 410 and 420. The electron transfer layer 430 may be formed of, for example, a gelatinized potassium ferricyanide solution.

The electron generating capsule 440 is formed in, for example, a substantially spherical shape having the diameter of 200 μm and has a structure in which a content liquid 443 containing glucose oxidase and PMEH is enclosed by an outer membrane 441 formed of sucrose. For example, three concave structures in the electron transfer layer 430 may each retain one electron generating capsule 440 in its inside.

In such an enzyme sensor 4, first, the sucrase to be detected and the sucrose contained in the outer membrane 441 are reacted to produce glucose and fructose. Next, glucose oxidase, which is contained in the content liquid 443 and oozes to the outer membrane 441 by the difference of the osmotic pressure, and the glucose are reacted to take out the electron from the glucose. Further, the electron taken out from the glucose is accepted by the ferricyanide ion or the like contained in the electron transfer layer 430. In this manner, the ferricyanide ion is converted to the ferrocyanide ion.

The above reactions are represented by the following chemical formulas 5 and 6.

[Chem. 3]

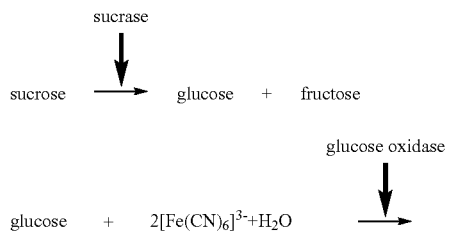

chemical formula 5 chemical formula 6

Thus, in the enzyme sensor 4, the logic portion 450 can read the electric current value corresponding to the amount of the sucrase by applying a positive-negative pulse voltage of 400 mV for about 1 second between the pair of electrodes 410 and 420. Note that the enzyme sensor 4 may detect the amount of the sucrase in the period of 32 seconds by allowing about 30 seconds for the sucrase enzymatic reaction.

4. Summary

As described above, the enzyme sensor according to the first embodiment of the present disclosure converts the presence of the enzyme to be detected to the electric current by the reversible mechanism in which the electron is accepted by and released from the electrolyte, and thus can accurately measure the amount of the enzyme to be detected.

Further, the electronic device according to the second embodiment of the present disclosure determines the mental or physical state of the subject wearing the enzyme sensor on the basis of the enzyme amount measured by the enzyme sensor, and thus can output the driving corresponding to the mental or physical state of the subject.

Note that, in the above description, amylase, lipase, and sucrase are mentioned as the specific examples of the enzymes to be detected, however, the technique according to the present disclosure is not limited to such examples. The enzyme sensor according to one embodiment of the present disclosure can be used to detect other enzymes by changing the substrate contained in the outer membrane of the electron generating capsule.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An enzyme sensor including:
a pair of electrodes;
an electron transfer layer held between the pair of electrodes; and
an electron generating capsule in which a membrane containing at least a substrate of an enzyme to be detected encloses at least one or more kinds of enzymes other than the enzyme to be detected, the electron generating capsule being in contact with the electron transfer layer.

(2)
The enzyme sensor according to (1), in which the electron generating capsule encloses an enzyme that oxidizes an enzymatic reaction product generated from the substrate through at least one or more steps.

(3)
The enzyme sensor according to (1) or (2), in which the electron generating capsule has a substantially spherical shape.

(4)
The enzyme sensor according to any one of (1) to (3), in which the electron transfer layer includes an electrolyte that can accept an electron.

(5)
The enzyme sensor according to (4), in which the electron transfer layer is a layer formed by gelatinating a solution containing the electrolyte.

(6)

The enzyme sensor according to any one of (1) to (5), in which a concave structure is provided in the electron transfer layer, and the electron generating capsule is retained inside the concave structure.

(7)

The enzyme sensor according to (6), in which at least an opening of the concave structure is covered with an ion exchange membrane.

(8)

The enzyme sensor according to (6) or (7), in which a plurality of the concave structures is provided on one surface of the electron transfer layer and each opening of the concave structures is closed by a movable shielding plate, and the shielding plate is configured to open each opening of the concave structures on the basis of a state of the electron generating capsule.

(9)

The enzyme sensor according to any one of (1) to (8), further including a detection portion that acquires a detection signal of the enzyme to be detected, in which the detection portion acquires the detection signal by applying a pulse voltage between the pair of electrodes.

(10)

The enzyme sensor according to (9), in which the pulse voltage is a positive-negative pulse voltage having a symmetrical rectangular waveform.

(11)

The enzyme sensor according to (9) or (10), in which the detection signal is acquired at a predetermined time interval, and the detection signal is an electric current having a level corresponding to an amount of the enzyme to be detected.

(12)

The enzyme sensor according to any one of (1) to (11), in which the enzyme to be detected is amylase, the substrate contained in the membrane of the electron generating capsule is starch, and the enzyme enclosed in the electron generating capsule includes at least maltase and glucose oxidase.

(13)

An electronic device including:

an enzyme sensor that includes a pair of electrodes, an electron transfer layer held between the pair of electrodes, and an electron generating capsule in which a membrane containing at least a substrate of an enzyme to be detected encloses at least one or more kinds of enzymes other than the enzyme to be detected, the electron generating capsule being in contact with the electron transfer layer;

a determination portion that determines a state of a wearing subject wearing the enzyme sensor on the basis of an amount of the enzyme detected by the enzyme sensor; and a driving portion that performs driving on the basis of the determined state of the wearing subject.

(14)

The electronic device according to (13), in which the driving by the driving portion includes at least one of text display, image display, audio playback, music playback, a light emitting operation, a release of a compound, or a mechanical operation.

(15)

The electronic device according to (13) or (14), in which the driving portion leads the state of the wearing subject to a specific state by the driving.

REFERENCE SIGNS LIST 1 enzyme sensor
100 sensor portion
110,120 electrodes
130 electron transfer layer
140 electron generating capsule
141 outer membrane
143 content liquid
150 logic portion
151 voltage control portion
153 detection portion
155 alert portion
157 output portion
160 determination portion
170 driving portion
1000 electronic device

The invention claimed is:

1. An enzyme sensor, comprising:

a pair of electrodes;

an electron transfer layer held between the pair of electrodes; and an electron generating capsule in which a membrane containing a substrate of an enzyme to be detected encloses at least one or more kinds of enzymes other than the enzyme to be detected, wherein the electron generating capsule is in contact with the electron transfer layer.

2. The enzyme sensor according to claim 1, wherein an enzyme, of the at least one or more kinds of enzymes, oxidizes an enzymatic reaction product generated from the substrate.

3. The enzyme sensor according to claim 1, wherein the electron generating capsule has a substantially spherical shape.

4. The enzyme sensor according to claim 1, wherein the electron transfer layer includes an electrolyte that can accept an electron.

5. The enzyme sensor according to claim 4, wherein the electron transfer layer is a layer formed by gelatinating a solution containing the electrolyte.

6. The enzyme sensor according to claim 1, wherein a concave structure is provided in the electron transfer layer, and the electron generating capsule is retained inside the concave structure.

7. The enzyme sensor according to claim 6, wherein at least an opening of the concave structure is covered with an ion exchange membrane.

8. The enzyme sensor according to claim 6, wherein the concave structure is part of a plurality of concave structures provided on one surface of the electron transfer layer and each opening of the plurality of concave structures is closed by a movable shielding plate, and the movable shielding plate is configured to open each opening of the plurality of concave structures on a basis of a state of the electron generating capsule.

9. The enzyme sensor according to claim 1, further comprising
   a detection portion that acquires a detection signal of the enzyme to be detected, wherein
   the detection portion acquires the detection signal by applying a pulse voltage between the pair of electrodes.

10. The enzyme sensor according to claim 9, wherein the pulse voltage is a positive-negative pulse voltage having a symmetrical rectangular waveform.

11. The enzyme sensor according to claim 9, wherein
   the detection signal is acquired at a predetermined time interval, and
   the detection signal is an electric current having a level corresponding to an amount of the enzyme to be detected.

12. The enzyme sensor according to claim 1, wherein
   the enzyme to be detected is amylase,
   the substrate contained in the membrane of the electron generating capsule is starch, and
   an enzyme, of the at least one or more kinds of enzymes, enclosed in the electron generating capsule includes at least maltase and glucose oxidase.

13. An electronic device, comprising:
   an enzyme sensor that includes
      a pair of electrodes,
      an electron transfer layer held between the pair of electrodes, and
      an electron generating capsule in which a membrane containing a substrate of an enzyme to be detected encloses at least one or more kinds of enzymes other than the enzyme to be detected, wherein the electron generating capsule is in contact with the electron transfer layer;
   a determination portion that determines a state of a subject wearing the enzyme sensor on a basis of an amount of the enzyme detected by the enzyme sensor; and
   a driving portion that drives an output, on a basis of the determined state of the subject.

14. The electronic device according to claim 13, wherein the output by the driving portion includes at least one of text display, image display, audio playback, music playback, a light emitting operation, a release of a compound, or a mechanical operation.

15. The electronic device according to claim 13, wherein the driving portion leads the state of the subject to a specific state by the output.

\* \* \* \* \*